United States Patent
U'Ren et al.

(10) Patent No.: US 9,625,360 B2
(45) Date of Patent: *Apr. 18, 2017

(54) APPARATUS, SYSTEM, AND METHOD FOR COLLECTING A TARGET MATERIAL

(71) Applicant: RareCyte, Inc., Seattle, WA (US)

(72) Inventors: Lance U'Ren, Seattle, WA (US); Elizabeth Chang, Mercer Island, WA (US); Jennifer Chow, Seattle, WA (US)

(73) Assignee: RareCyte, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/883,071

(22) Filed: Oct. 14, 2015

(65) Prior Publication Data
US 2016/0041077 A1    Feb. 11, 2016

Related U.S. Application Data

(63) Continuation-in-part of application No. 14/495,449, filed on Sep. 24, 2014, now Pat. No. 9,039,999, which
(Continued)

(51) Int. Cl.
*G01N 1/40* (2006.01)
*B01L 3/00* (2006.01)
(Continued)

(52) U.S. Cl.
CPC ......... *G01N 1/4077* (2013.01); *B01D 21/262* (2013.01); *B01L 3/5021* (2013.01);
(Continued)

(58) Field of Classification Search
CPC ............ B01D 21/262; B01L 2200/026; B01L 2200/0631; B01L 2200/0689;
(Continued)

(56) References Cited

U.S. PATENT DOCUMENTS 5,560,830 A * 10/1996 Coleman ............. B01L 3/50215
  210/121
5,646,004 A    7/1997 Van Vasselaer
(Continued)

FOREIGN PATENT DOCUMENTS

WO    WO 2012/0149641 A1    11/2012

OTHER PUBLICATIONS

Axis-Shield, OptiPrep Leaflet.

*Primary Examiner* — Maureen Wallenhorst
(74) *Attorney, Agent, or Firm* — Olympic Patent Works PLLC

(57) ABSTRACT

This disclosure is directed to an apparatus, system and method for retrieving a target material from a sample. A fraction-density-altering solution may be added to a vessel that contains the sample to change the density of a first fraction of the sample without changing the density of the target material or the density of any other sample fraction. A collector may be inserted into the vessel to funnel the target material from the sample into the collector or into a processing receptacle included in the collector. In one implementation, the collector may include a cannula which extends from a funnel into a chamber to hold the processing receptacle. In another implementation, the processing receptacle may be inserted into a bore within the collector.

19 Claims, 31 Drawing Sheets

Related U.S. Application Data is a continuation-in-part of application No. 14/090,337, filed on Nov. 26, 2013, now abandoned, application No. 14/883,071, which is a continuation-in-part of application No. 14/266,939, filed on May 1, 2014, now abandoned, said application No. 14/665,368 is a continuation-in-part of application No. 14/610,522, filed on Jan. 30, 2015, now Pat. No. 9,539,570, and a continuation-in-part of application No. 14/665,368, filed on Mar. 23, 2015, now Pat. No. 9,217,697.

(60) Provisional application No. 61/732,029, filed on Nov. 30, 2012, provisional application No. 61/745,094, filed on Dec. 21, 2012, provisional application No. 61/791,883, filed on Mar. 15, 2013, provisional application No. 61/818,301, filed on May 1, 2013, provisional application No. 61/869,866, filed on Aug. 26, 2013, provisional application No. 61/935,457, filed on Feb. 4, 2014, provisional application No. 62/068,480, filed on Oct. 24, 2014.

(51) Int. Cl.
*C12Q 1/68* (2006.01)
*B01D 21/26* (2006.01)
*G01N 1/34* (2006.01)
*B01L 9/00* (2006.01)

(52) U.S. Cl.
CPC ......... *B01L 3/50215* (2013.01); *B01L 3/5635* (2013.01); *C12Q 1/6806* (2013.01); *G01N 1/34* (2013.01); *B01L 9/50* (2013.01); *B01L 2200/026* (2013.01); *B01L 2200/0631* (2013.01); *B01L 2200/0689* (2013.01); *B01L 2300/042* (2013.01); *B01L 2300/0672* (2013.01); *B01L 2300/0851* (2013.01); *B01L 2400/0683* (2013.01); *Y10T 436/25375* (2015.01)

(58) Field of Classification Search
CPC ....... B01L 2300/042; B01L 2300/0672; B01L 2300/0851; B01L 2400/0683; B01L 3/5021; B01L 3/50215; B01L 3/5635; B01L 9/50; C12Q 1/6806; G01N 1/34; G01N 1/4077; Y10T 436/25; Y10T 436/25125; Y10T 436/25375; Y10T 436/2575
USPC ..... 436/43, 45, 63, 164, 172, 174, 175, 177, 436/180, 501; 422/72, 82.08, 527, 533; 435/29, 30, 6.11, 6.12, 7.92
See application file for complete search history.

(56) References Cited

U.S. PATENT DOCUMENTS

| | | | |
|---|---|---|---|
| 6,479,298 B1* | 11/2002 | Miller | B01L 3/50215 210/121 |
| 8,394,342 B2* | 3/2013 | Felix | B01L 3/50215 210/513 |
| 9,039,999 B2* | 5/2015 | Campton | B01D 21/262 422/533 |
| 9,217,697 B2* | 12/2015 | U'Ren | G01N 1/4077 |
| 2006/0263266 A1* | 11/2006 | DiCesare | B01L 3/50215 422/533 |
| 2010/0317106 A1* | 12/2010 | Levine | G01N 33/491 435/372 |
| 2013/0315798 A1* | 11/2013 | Crawford | B01L 3/50215 422/533 |

* cited by examiner

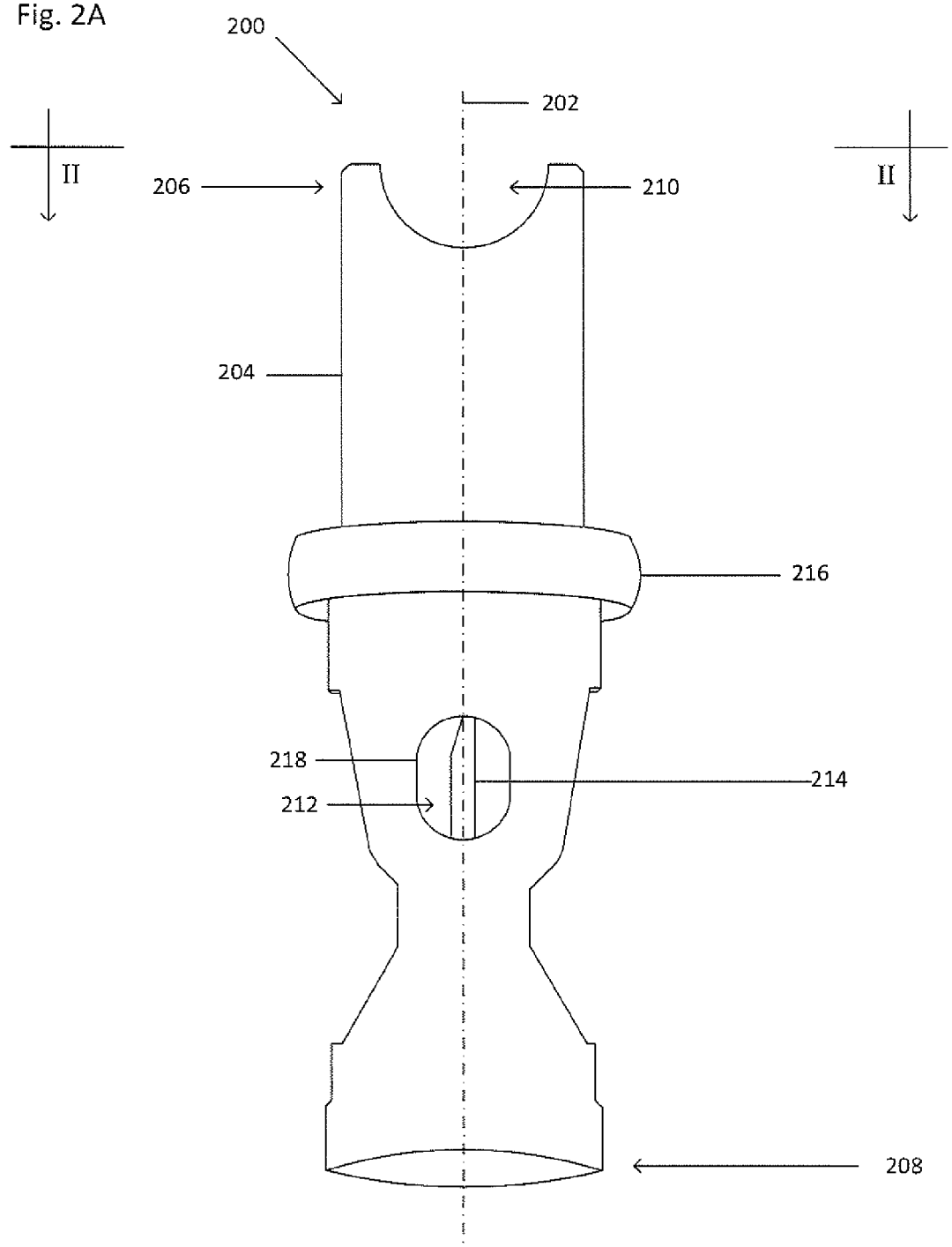

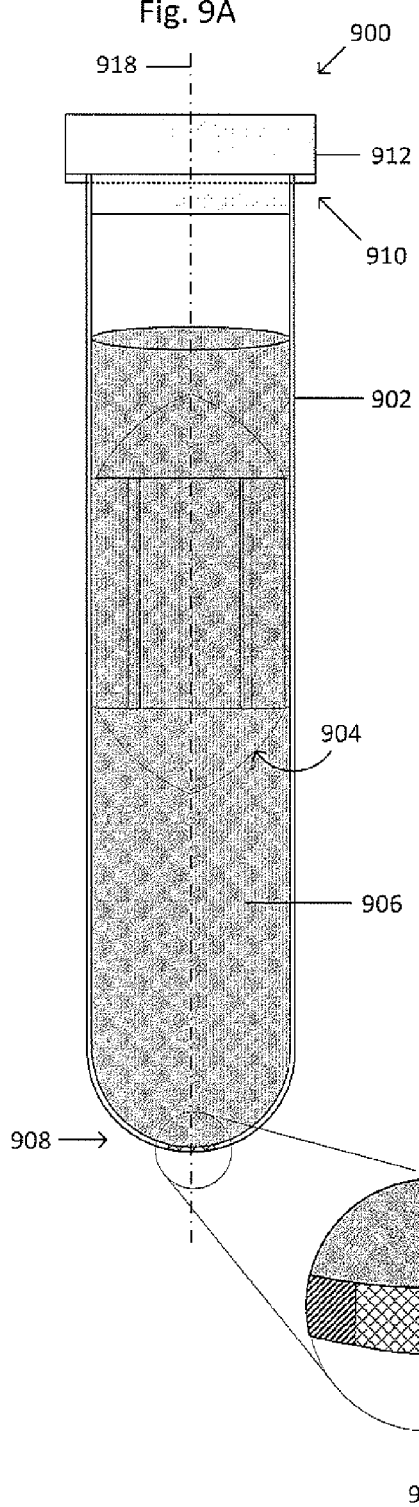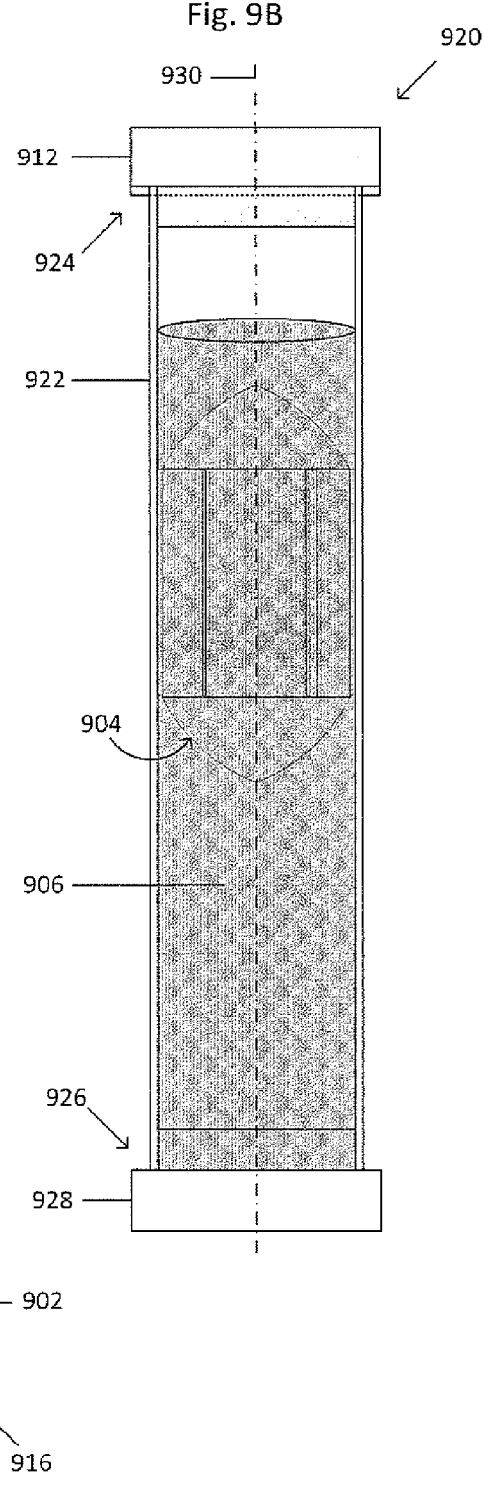

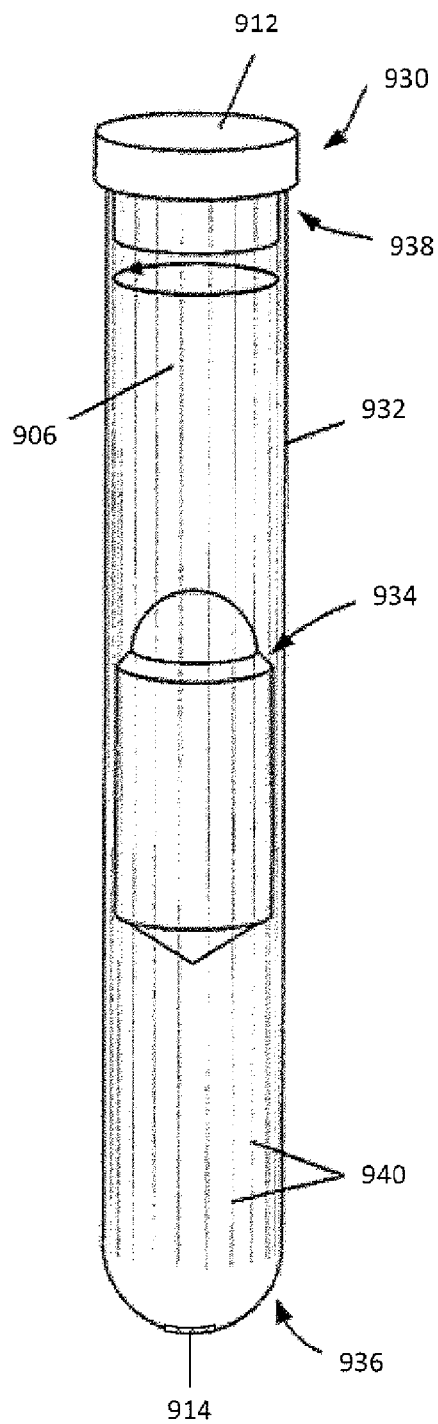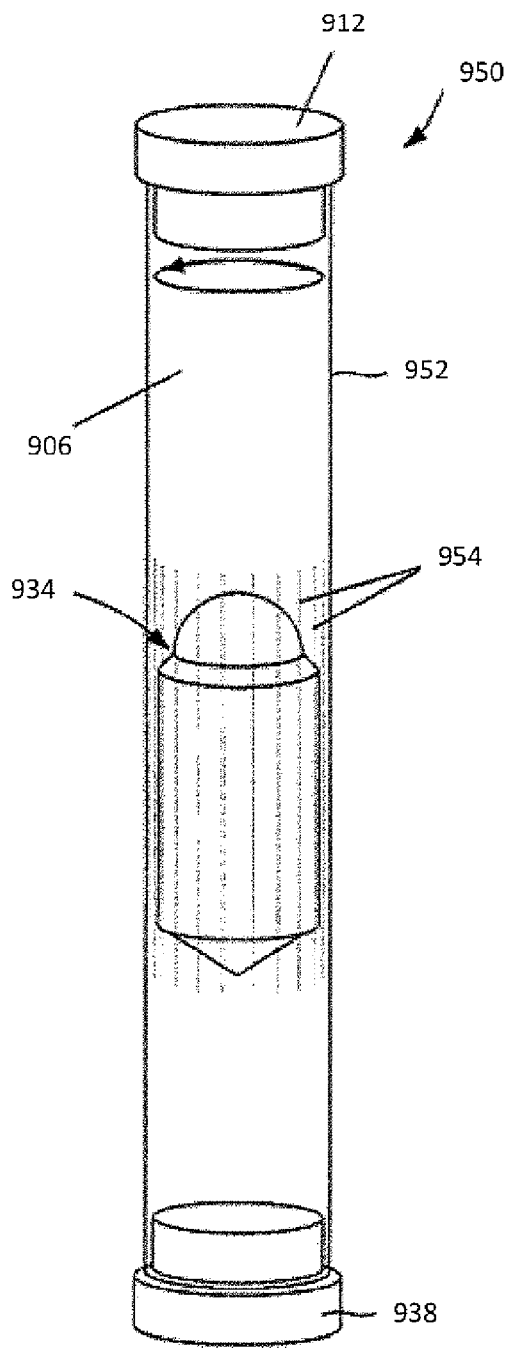

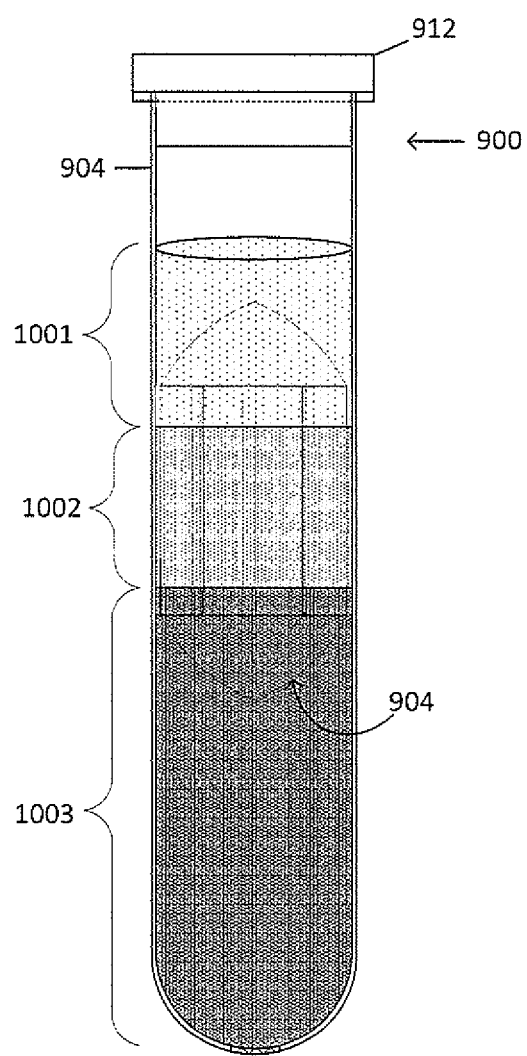

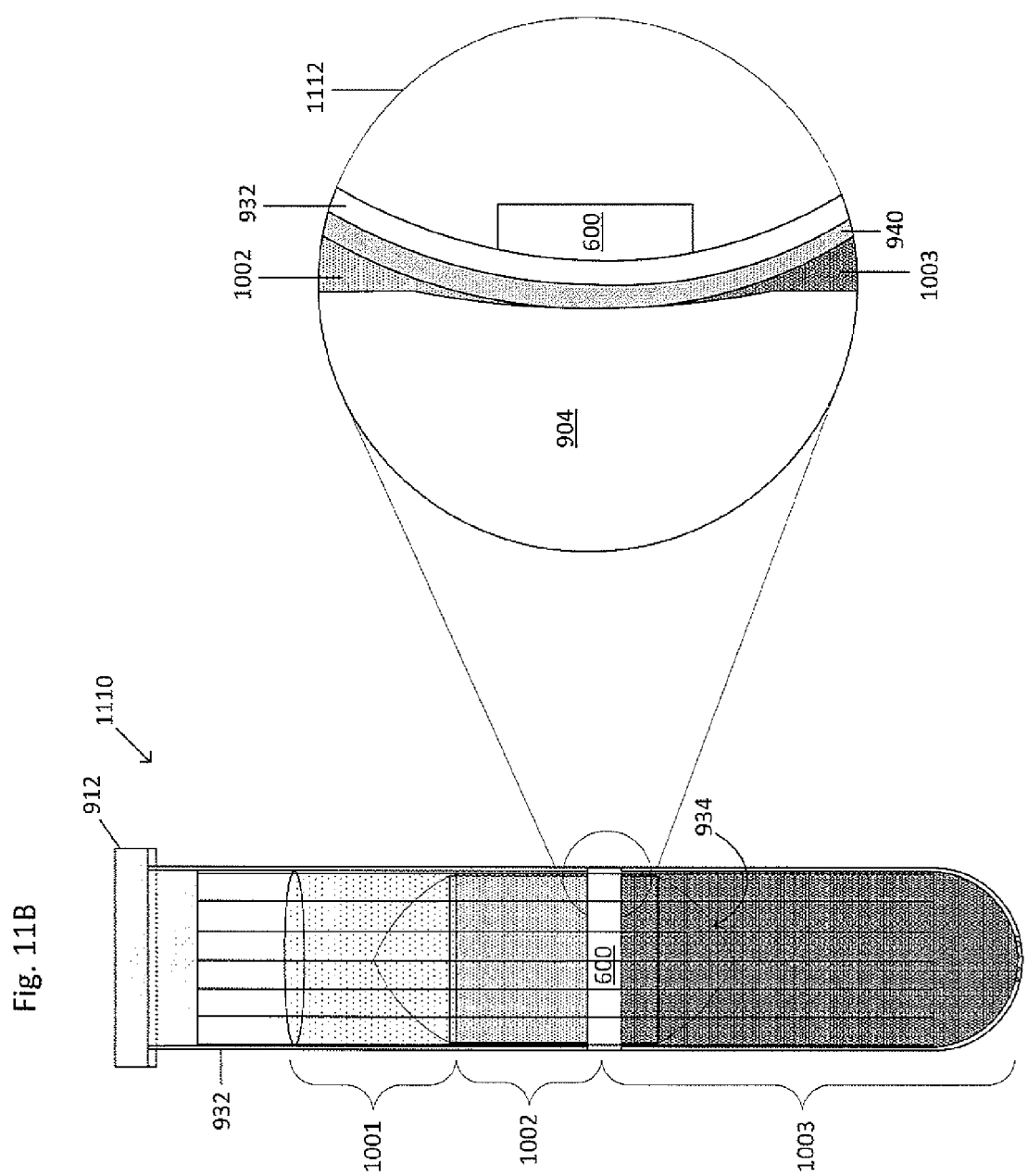

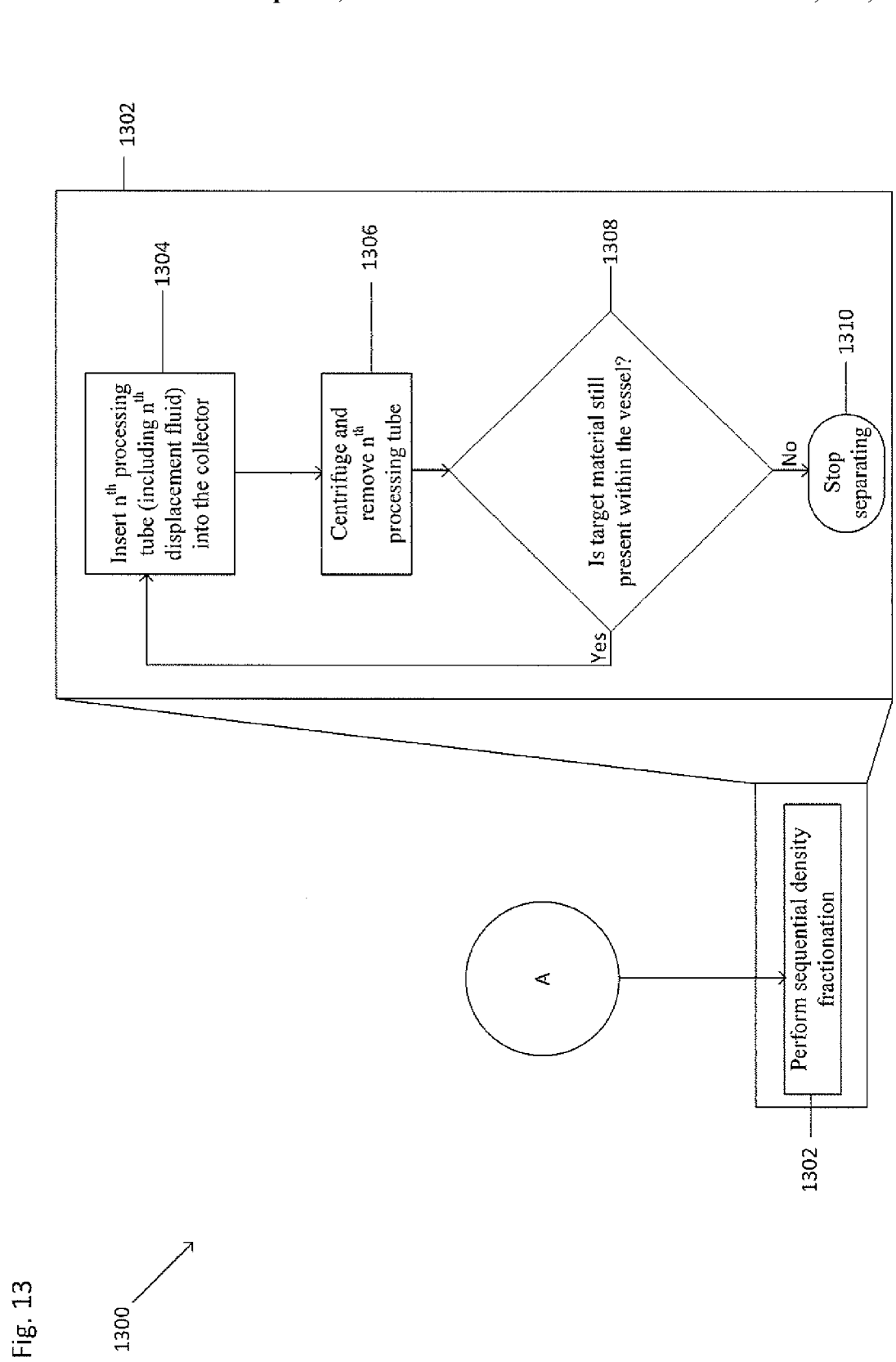

APPARATUS, SYSTEM, AND METHOD FOR COLLECTING A TARGET MATERIAL

CROSS-REFERENCE TO A RELATED APPLICATION

This application claims the benefit of Provisional Application No. 62/068,480, filed Oct. 24, 2014; and this application is a continuation-in-part of application Ser. No. 14/665,368, filed Mar. 23, 2015, (now U.S. Pat. No. 9,217,687) which is a continuation-in-part of application Ser. No. 14/610,522, filed Jan. 30, 2015, which claims the benefit of Provisional Application No. 61/935,457, filed Feb. 4, 2014, and which is also a continuation-in-part of application Ser. No. 14/495,449, filed Sep. 24, 2014, (now U.S. Pat. No. 9,039,999) which is a continuation-in-part of application Ser. No. 14/090,337, filed Nov. 26, 2013, (now abandoned) which claims the benefit of Provisional Application No. 61/732,029, filed Nov. 30, 2012; Provisional Application No. 61/745,094, filed Dec. 21, 2012; Provisional Application No. 61/791,883, filed Mar. 15, 2013; Provisional Application No. 61/818,301, filed May 1, 2013; and Provisional Application No. 61/869,866, filed Aug. 26, 2013; and is also a continuation-in-part of application Ser. No. 14/266,939, filed May 1, 2014, (now abandoned) which claims the benefit of Provisional Application No. Provisional Application No. 61/818,301, filed May 1, 2013, Provisional Application No. 61/869,866, filed Aug. 26, 2013, and Provisional Application No. 61/935,457, filed Feb. 4, 2014.

TECHNICAL FIELD

This disclosure relates generally to density-based fluid separation and, in particular, to retrieving a target material from a suspension.

BACKGROUND

Suspensions often include materials of interests that are difficult to detect, extract and isolate for analysis. For instance, whole blood is a suspension of materials in a fluid. The materials include billions of red and white blood cells and platelets in a proteinaceous fluid called plasma. Whole blood is routinely examined for the presence of abnormal organisms or cells, such as ova, fetal cells, endothelial cells, parasites, bacteria, and inflammatory cells, and viruses, including HIV, cytomegalovirus, hepatitis C virus, and Epstein-Barr virus. Currently, practitioners, researchers, and those working with blood samples try to separate, isolate, and extract certain components of a peripheral blood sample for examination. Typical techniques used to analyze a blood sample include the steps of smearing a film of blood on a slide and staining the film in a way that enables certain components to be examined by bright field microscopy.

On the other hand, materials of interest that occur in a suspension with very low concentrations are especially difficult if not impossible to detect and analyze using many existing techniques. Consider, for instance, circulating tumor cells ("CTCs"), which are cancer cells that have detached from a tumor, circulate in the bloodstream, and may be regarded as seeds for subsequent growth of additional tumors (i.e., metastasis) in different tissues. The ability to accurately detect and analyze CTCs is of particular interest to oncologists and cancer researchers. However, CTCs occur in very low numbers in peripheral whole blood samples. For instance, a 7.5 ml sample of peripheral whole blood sample that contains as few as 5 CTCs is considered clinically relevant for the diagnosis and treatment of a cancer patient. In other words, detecting 5 CTCs in a 7.5 ml blood sample is equivalent to detecting 1 CTC in a background of about 40-60 billion red and white blood cells, which is extremely time consuming, costly and difficult to accomplish using blood film analysis.

As a result, practitioners, researchers, and those working with suspensions continue to seek systems and methods for accurate analysis of suspensions for the presence or absence rare materials of interest.

DESCRIPTION OF THE DRAWINGS

FIGS. 2A-2B show an example collector.
FIGS. 9A-9D show example float and tube systems.
FIG. 10 shows a sample having undergone density-based separation.
FIGS. 11A-11B show a seal being formed by a clamp.
FIG. 13 shows a flow diagram of an example method for retrieving a target material.

DETAILED DESCRIPTION

This disclosure is directed to an apparatus, system and method for retrieving a target material from a suspension. A system includes a processing vessel, such as an Eppendorf tube, a syringe or a test tube, and a collector. The collector is sized and shaped to fit into a primary vessel, such as a test tube. The collector funnels the target material from the suspension through a cannula and into the processing vessel. The cannula extends into a cavity at a first end of the collector that holds the processing vessel. The collector includes a funnel at a second end in fluid communication with the cannula. In one implementation, the processing vessel includes at least one collection fluid to be expelled, such that the at least one collection fluid pushes the target material into the collector.

Collector

Figure 1A:
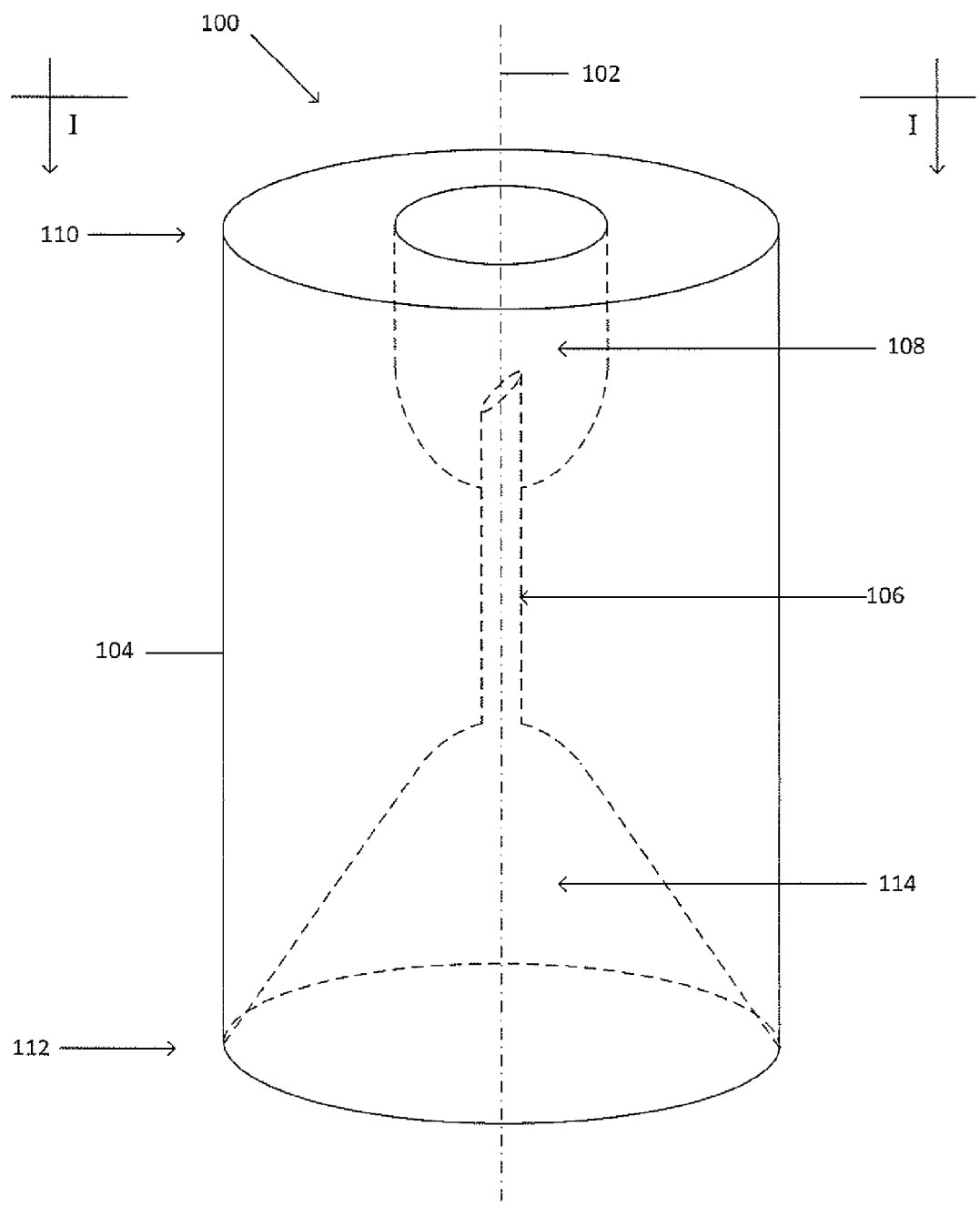
FIGS. 1A-1B show an example collector.
Figure 1B:
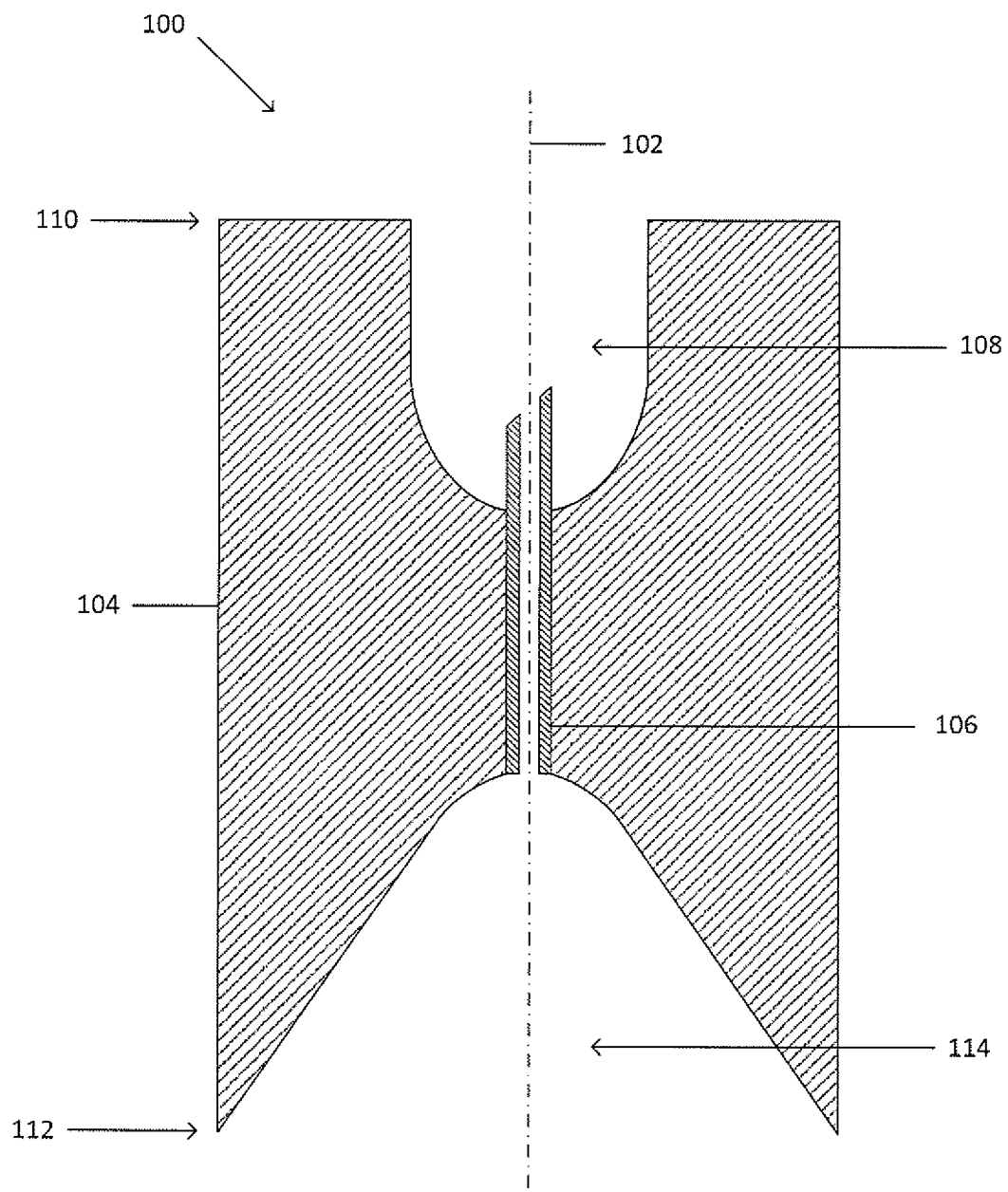

FIG. 1A shows an isometric view of a collector 100. FIG. 1B shows a cross-sectional view of the collector 100 taken along the line I-I shown in FIG. 1A. Dot-dashed line 102 represents the central or highest-symmetry axis of the collector 100. The collector 100 may be sized and shaped to fit within a primary vessel containing or capable of holding a suspension, the suspension suspected of including a target material. The collector 100 funnels the target material from the suspension through a cannula 106 and into a processing vessel (not shown) to be located within a cavity 108. The collector 100 includes the main body 104 which includes a first end 110 and a second end 112. A seal may be formed between the second end 112 and an inner wall of the primary vessel to maintain a fluid-tight sealing engagement before, during, and after centrifugation and to inhibit any portion of the suspension from being located or flowing between an inner wall of the primary vessel and a main body 104 of the collector 100. The seal may be formed by an interference fit, a grease (such as vacuum grease), an adhesive, an epoxy, by bonding (such as by thermal bonding), by welding (such as by ultrasonic welding), by clamping (such as with a ring or clamp), an insert (such as an O-ring or a collar) that fits between the second end 112 and the inner wall of the primary vessel, or the like. The main body 104 may be any appropriate shape, including, but not limited to, cylindrical, triangular, square, rectangular, or the like. The collector 100 also includes an internal funnel 114 which is a concave opening. The funnel 114 may taper toward the cannula 106 from the second end 112. The funnel 114 channels a target material from below the second end 112 into the cannula 106 which is connected to, and in fluid communication with, an apex of the funnel 114. The apex of the funnel 114 has a smaller diameter than the mouth of the funnel 114. The funnel 114 is formed by a tapered wall that may be straight, curvilinear, arcuate, or the like. The funnel 114 may be any appropriate shape, including, but not limited to, tubular, spherical, domed, conical, rectangular, pyramidal, or the like. Furthermore, the outermost diameter or edge of the funnel 114 may be in continuous communication or constant contact (i.e. sit flush) with the inner wall of the primary vessel such that no dead space is present between the second end 112 of the collector 100 and the inner wall of the primary vessel.

The cannula 106, such as a tube or a needle, including, but not limited to a non-coring needle, extends from the apex of the funnel 114 and into the cavity 108. In the example of FIG. 1, the cavity 108 is a concave opening extending from the first end 110 into the main body 104 and may accept and support the processing vessel (not shown). The cavity 108 may be any appropriate depth to accept and support the processing vessel (not shown). The cannula 106 may extend any appropriate distance into the cavity 108 in order to puncture the base of, or be inserted into, the processing vessel (not shown). The cannula 106 may include a flat tip, a beveled tip, a sharpened tip, or a tapered tip. Furthermore, the cavity 108 may be any appropriate shape, including, but not limited to, tubular, spherical, domed, conical, rectangular, pyramidal, or the like. The cavity 108 may be threaded to engage a threaded portion of the processing vessel (not shown).

The collector 100 may also include a retainer (not shown) to prevent the collector 100 from sliding relative to the primary vessel, thereby keeping the collector 100 at a pre-determined height within the primary vessel. The retainer (not shown) may be a shoulder extending radially from the first end 110, a clip, a circular protrusion that extends beyond the circumference of the cylindrical main body 104, a detent, or the like.

Figure 2B:
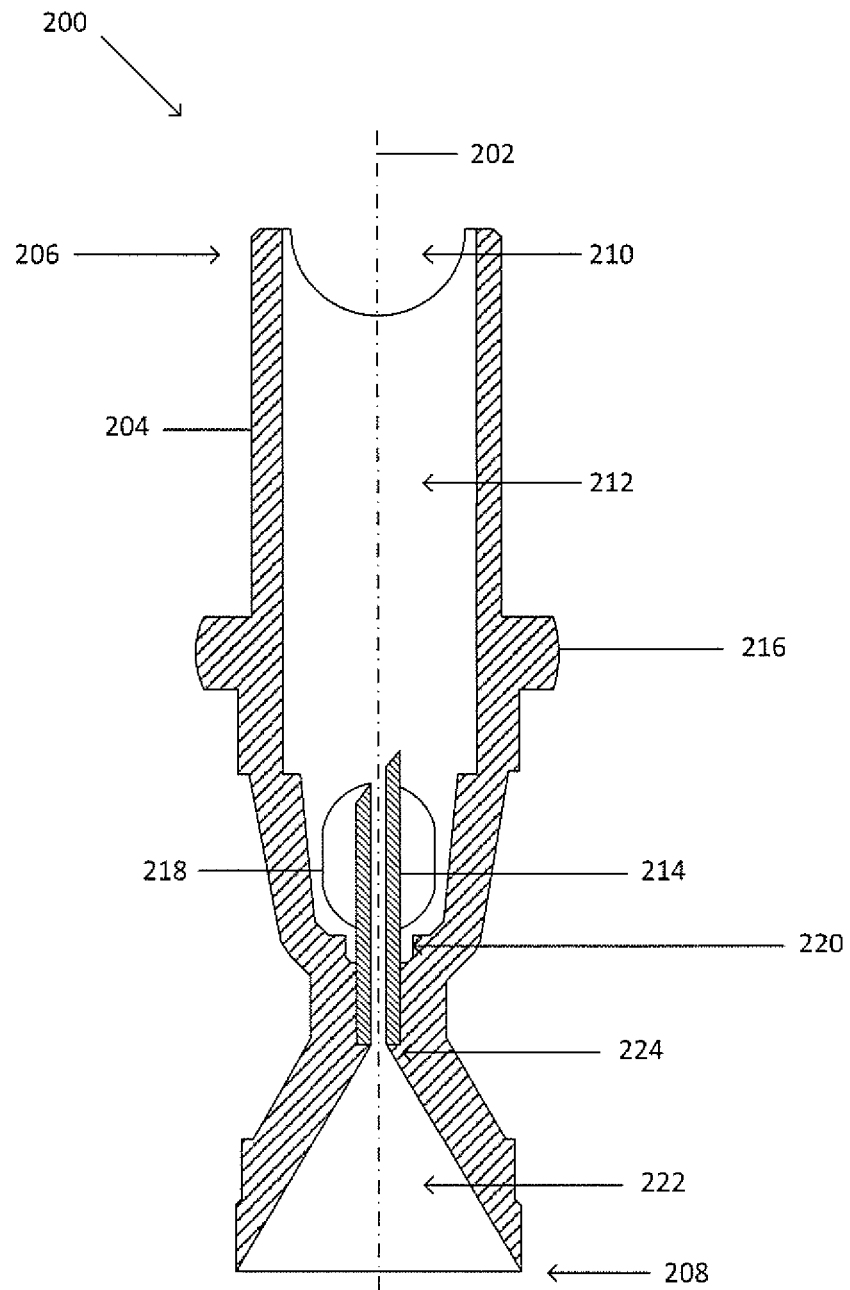

FIG. 2A shows an isometric view of a collector 200. FIG. 2B shows a cross-section view of the collector 200 taken along the line II-II shown in FIG. 2A. Dot-dashed line 202 represents the central or highest-symmetry axis of the collector 200. The collector 200 is similar to the collector 100, except that the collector 200 includes a main body 204 that is more elongated than the main body 104 of the collector 100 in order to accommodate a greater portion of the processing vessel (not shown). The main body 204 includes a first end 206 and a second end 208. A seal may be formed between the second end 208 and an inner wall of the primary vessel to maintain a fluid-tight sealing engagement before, during, and after centrifugation and to inhibit any portion of the suspension flowing between an inner wall of the primary vessel and the main body 204 of the collector 200. The seal may be formed by an interference fit, a grease (such as vacuum grease), an adhesive, an epoxy, by bonding (such as thermal bonding), by welding (such as ultrasonic welding), clamping (such as with a ring or clamp), an insert (such as an O-ring or a collar) that fits between the second end 208 and the inner wall of the primary vessel, or the like.

The first end 206 includes a cavity 212 dimensioned to accept and hold at least a portion of the processing vessel (not shown). The cavity 212 may have a tapered or stepped bottom end 220 on which the processing vessel (not shown) may rest. The first end 206 may also include at least one cut-out 210 to permit proper grip of the processing vessel (not shown) for insertion and removal. The collector 200 funnels the target material from the suspension into an internal funnel 222 at the second end 208, through a cannula 214, and into a processing vessel (not shown) located within the cavity 212. The cannula 214 may rest on a shelf 224 so that an inner bore of the cannula 214 sits flush with an inner wall of the funnel 222, as shown in FIG. 2B.

The collector 200 may include a shoulder 216, which extends circumferentially around the main body 204. The shoulder 216 may be larger than the inner diameter of the primary vessel so as to rest on the open end of the primary vessel and, upon applying a lock ring (not shown) to the outside of the primary vessel and the shoulder 216, to inhibit movement of the collector 200 relative to the primary vessel. The lock ring (not shown) applies pressure to the primary vessel along the shoulder 216. The lock ring may be a two-piece ring, a one piece ring wrapping around the full circumference of the primary vessel, or a one piece ring wrapping around less than the full circumference of the primary vessel, such as one-half (½), five-eighths (⅝), two-thirds (⅔), three-quarters (¾), seven-eighths (⅞), or the like. Alternatively, the shoulder 216 may fit within the primary vessel. Alternatively, the shoulder 216 may be a clip, such that the shoulder 216 may include a catch into which the primary vessel may be inserted to inhibit movement of the collector 200 relative to the primary vessel. Alternatively, the shoulder 216 may form an interference fit with the inner wall of the primary vessel around which a seal ring may be placed.

As shown in FIG. 2A, the collector 200 may include at least one window 218 to access the cavity 212 through an inner wall of the main body 204. The at least one window 218 permits an operator to confirm proper placement of the processing vessel (not shown) within the cavity 212. The at least one window 218 also allows fluid discharged from the cannula 214 to flow out of the collector 200 and into a space formed between the collector 200 and the primary vessel (not shown) and above the seal between the second end 208 and the inner wall of the primary vessel.

Figure 2C:
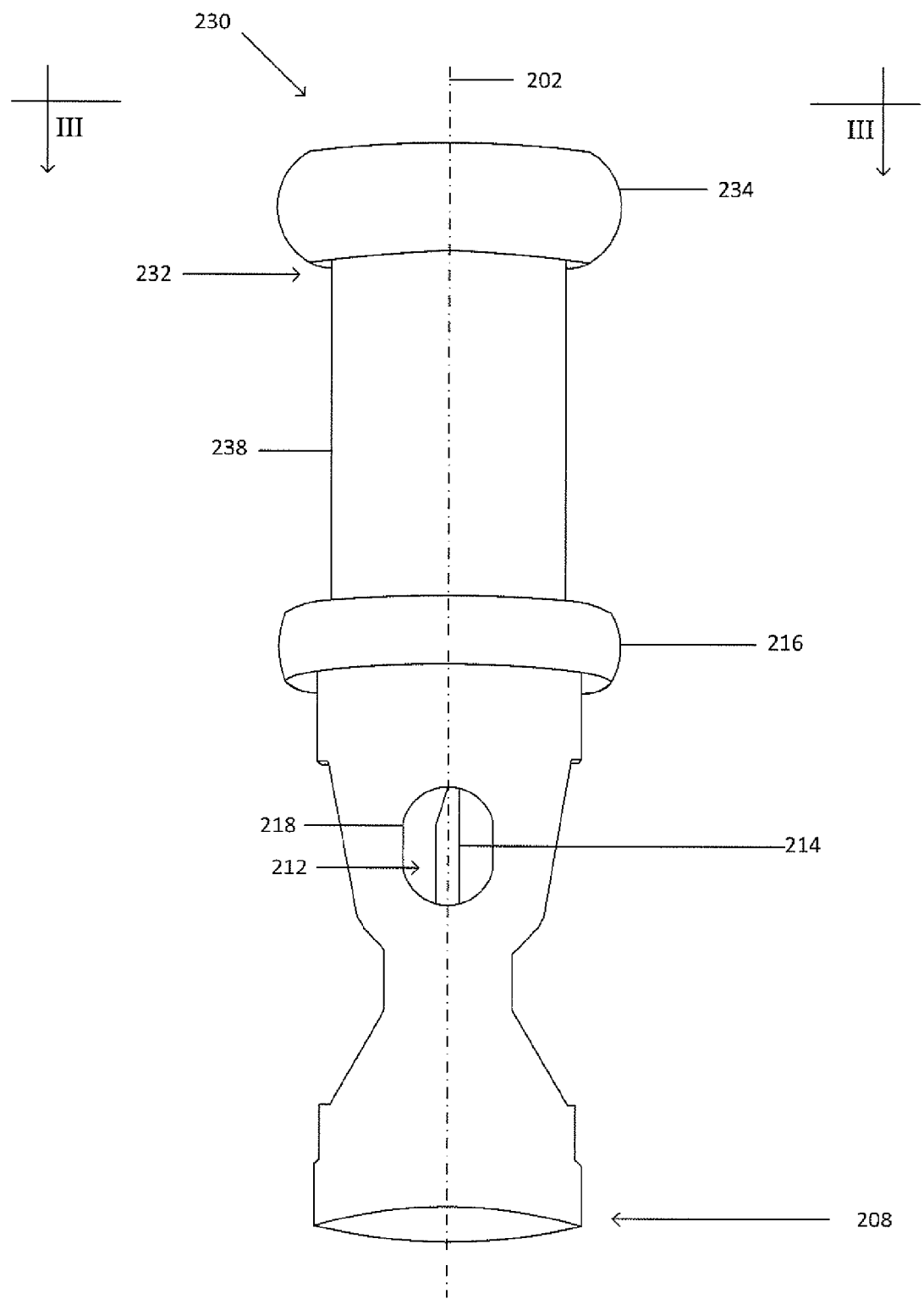
FIGS. 2C-2D show an example collector.
Figure 2D:
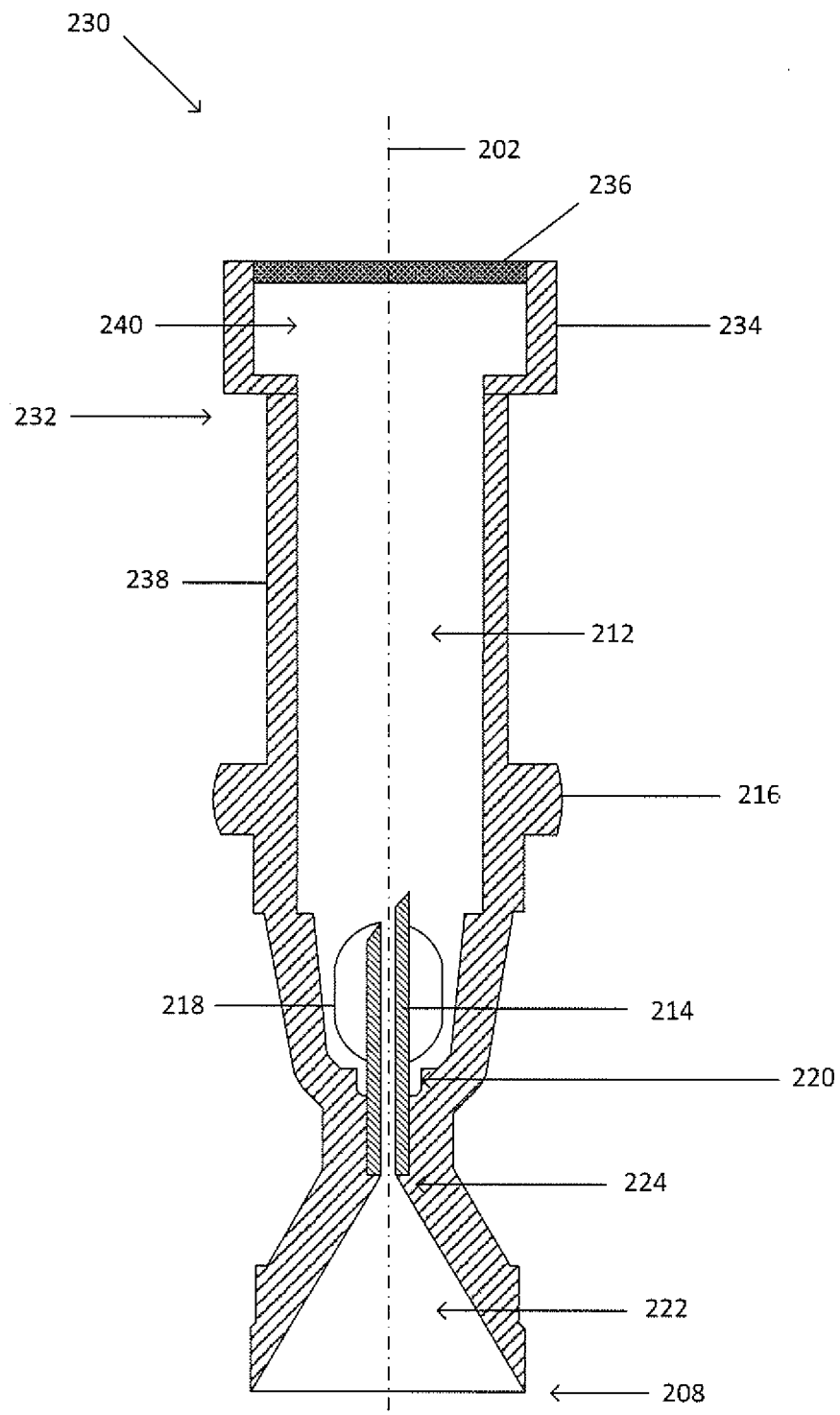

FIG. 2C shows an isometric view of a collector 230. FIG. 2D shows a cross-section view of the collector 230 taken along the line III-III shown in FIG. 2C. The collector 230 is similar to the collector 200, except that the collector 230 includes a main body 238 including an extension 234 extending away from a first end 232 and a lid 236 to at least temporarily seal an opening 240 within the extension 234. The opening 240 may be in fluid communication with the cavity 212 at the first end 232. The lid 236 may removable, puncturable and resealable (e.g. a flap lid), or puncturable and non-resealable (e.g. a foil lid). The extension 234 may be sized to accept the lid 236 when punctured such that a portion of the lid 236 does not extend into the cavity 212 at the first end 232. Note that the collector 230 does not include the at least one cut-out 210.

Figure 3A:
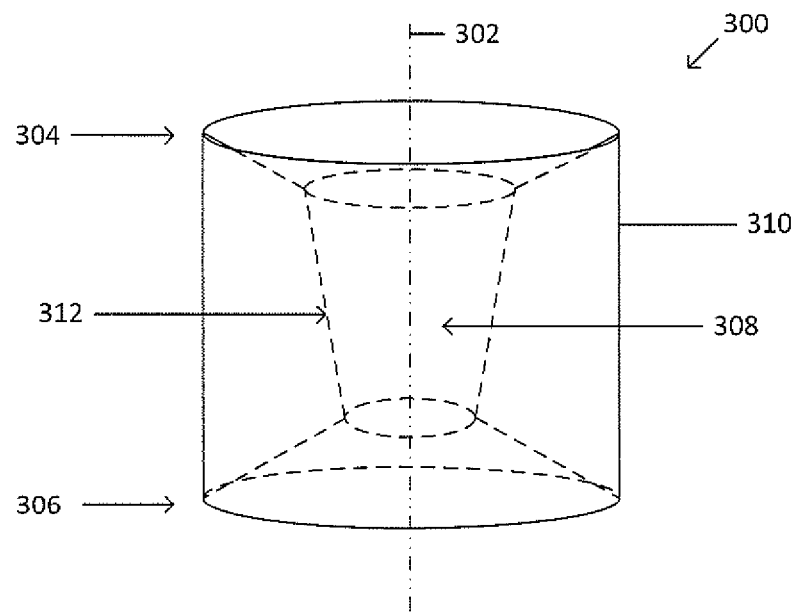
FIGS. 3A-3C show example collectors.

FIG. 3A shows an isometric view of a collector 300. Dot-dashed line 302 represents the central or highest-symmetry axis of the collector 300. The collector 300 includes a first side 304, a second side 306, and a bore 308. An inner wall 312 to form the bore 308, 324, and 334 may be tapered (i.e. becoming narrower from the first side 304 to the second side 306; or becoming wider from the first side 304 to the second 306), as shown in FIG. 3A.

The first and second sides 304 and 306 may be connected to the inner wall 312 via straight walls (i.e. first and second sides 304 and 306 are planar), tapered walls, or at least partially arcuate walls.

The collector 300 may be sized and shaped to fit within a vessel containing or capable of holding a suspension. The collector 300 fits against an inner wall of the vessel, such that no portion of the suspension may be located between the inner wall of the vessel and the main body 310 of the collector 300. The collector 300 gathers a sample within the bore 308. The bore 308 may be expandable, such that the diameter of the bore 308 may increase during centrifugation and then return to a resting diameter when not under centrifugation. Expanding the diameter may allow for less constricted flow of fluid and suspension components during centrifugation. The collector 300 may be composed of a ceramic, metal, polymer, flexible polymer, glass, organic or inorganic materials, or the like.

Figure 3B:
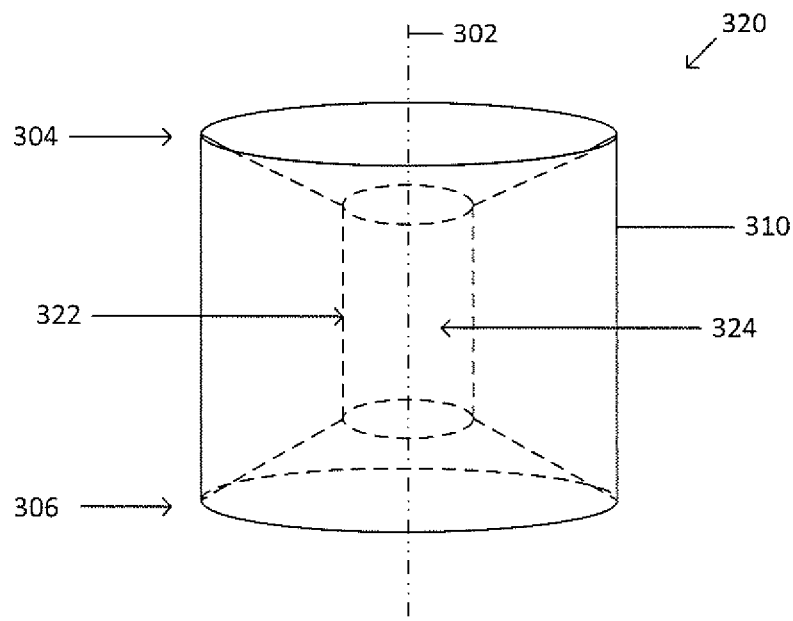
Figure 3C:
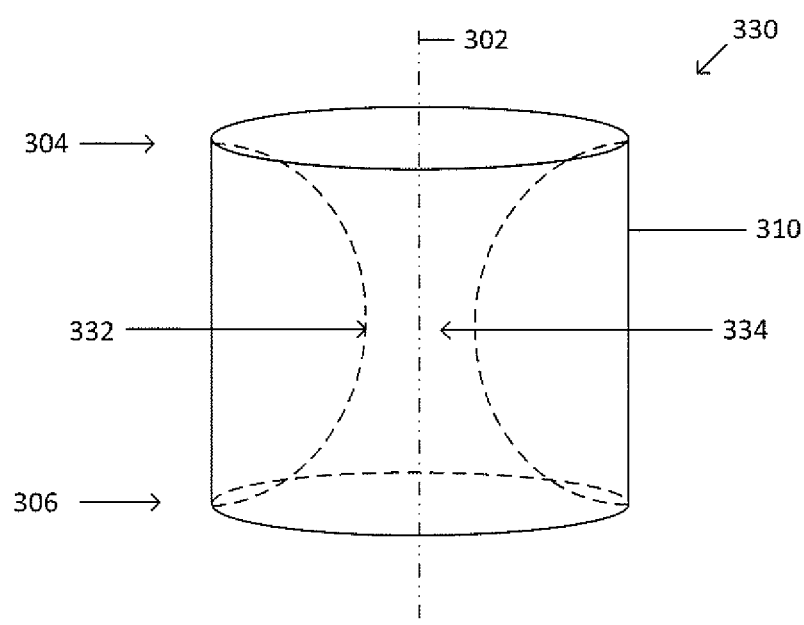

FIG. 3B shows an isometric view of a collector 320. The collector 320 is similar to the collector 300, except that an inner wall 322 of the collector 320 may be straight (i.e. having a uniform diameter from the first side 304 to the second side 306). FIG. 3C shows an isometric view of a collector 330. The collector 330 is similar to the collector 300, except that an inner wall 332 of the collector 330 may be at least partially arcuate (i.e. concave, convex, or curvilinear).

The collector may also include a filter (not shown). The filter (not shown) may be located at the second side or in the bore. The filter (not shown) is configured to provide a more pure sample by permitting a target material to pass through, while inhibiting non-target material from passing through.

The main body can be composed of a variety of different materials including, but not limited to, a ceramic; metals; organic or inorganic materials; and plastic materials, such as polyoxymethylene ("Delrin®"), polystyrene, acrylonitrile butadiene styrene ("ABS") copolymers, aromatic polycarbonates, aromatic polyesters, carboxymethylcellulose, ethyl cellulose, ethylene vinyl acetate copolymers, nylon, polyacetals, polyacetates, polyacrylonitrile and other nitrile resins, polyacrylonitrile-vinyl chloride copolymer, polyamides, aromatic polyamides ("aramids"), polyamide-imide, polyarylates, polyarylene oxides, polyarylene sulfides, polyarylsulfones, polybenzimidazole, polybutylene terephthalate, polycarbonates, polyester, polyester imides, polyether sulfones, polyetherimides, polyetherketones, polyetheretherketones, polyethylene terephthalate, polyamides, polymethacrylate, polyolefins (e.g., polyethylene, polypropylene), polyallomers, polyoxadiazole, polyparaxylene, polyphenylene oxides (PPO), modified PPOs, polystyrene, polysulfone, fluorine containing polymer such as polytetrafluoroethylene, polyurethane, polyvinyl acetate, polyvinyl alcohol, polyvinyl halides such as polyvinyl chloride, polyvinyl chloride-vinyl acetate copolymer, polyvinyl pyrrolidone, polyvinylidene chloride, specialty polymers, polystyrene, polycarbonate, polypropylene, acrylonitrite butadiene-styrene copolymer, butyl rubber, ethylene propylene diene monomer; and combinations thereof.

The cannula can be composed of a variety of different materials including, but not limited to, a ceramic; metals; organic or inorganic materials; and plastic materials, such as a polypropylene, acrylic, polycarbonate, or the like; and combinations thereof. The cannula may have a tip along a longitudinal axis of the cannula.

Collector-Processing Vessel System

Figure 4A:
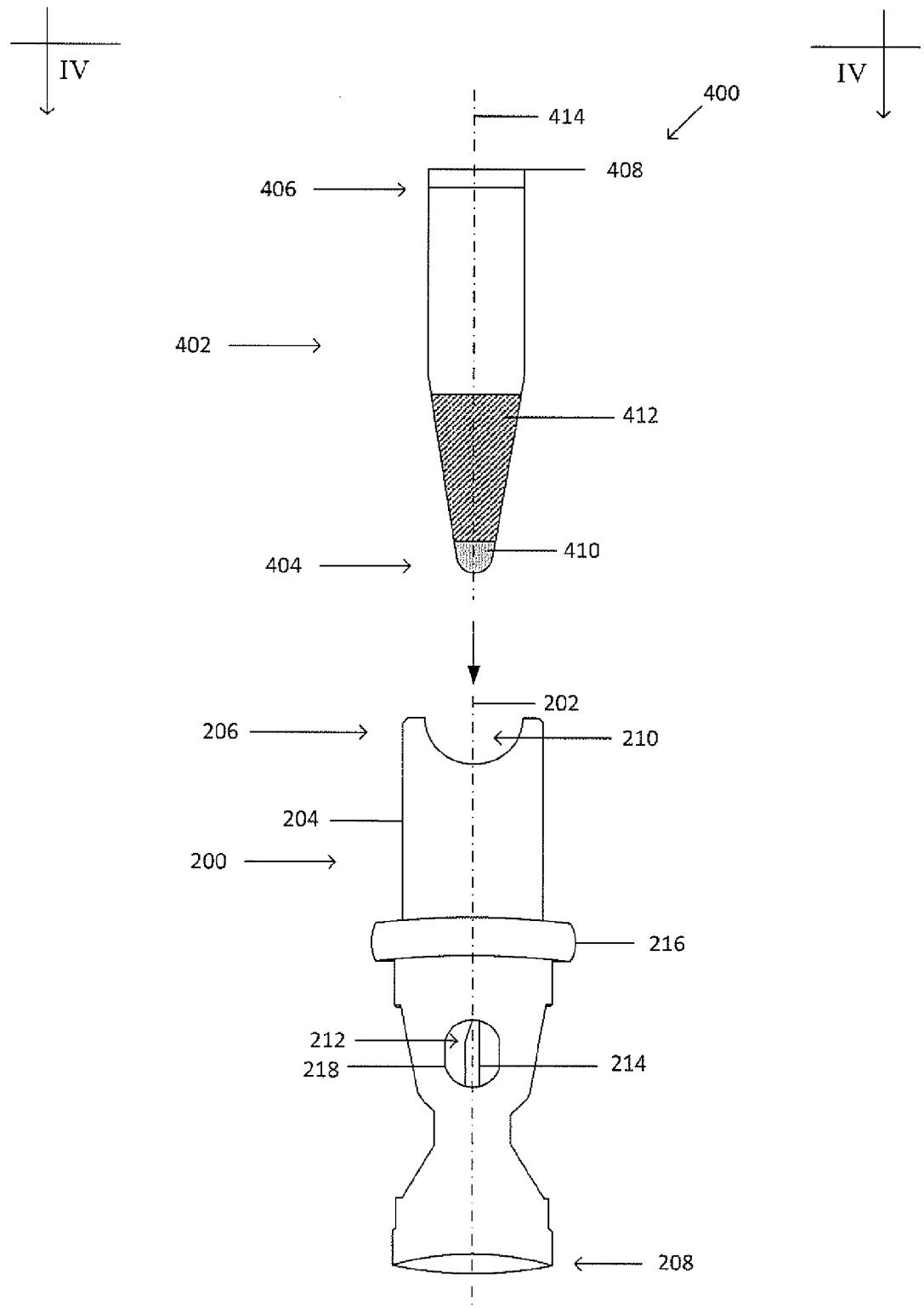
FIGS. 4A-4B show an example collector-processing vessel system.
Figure 4B:
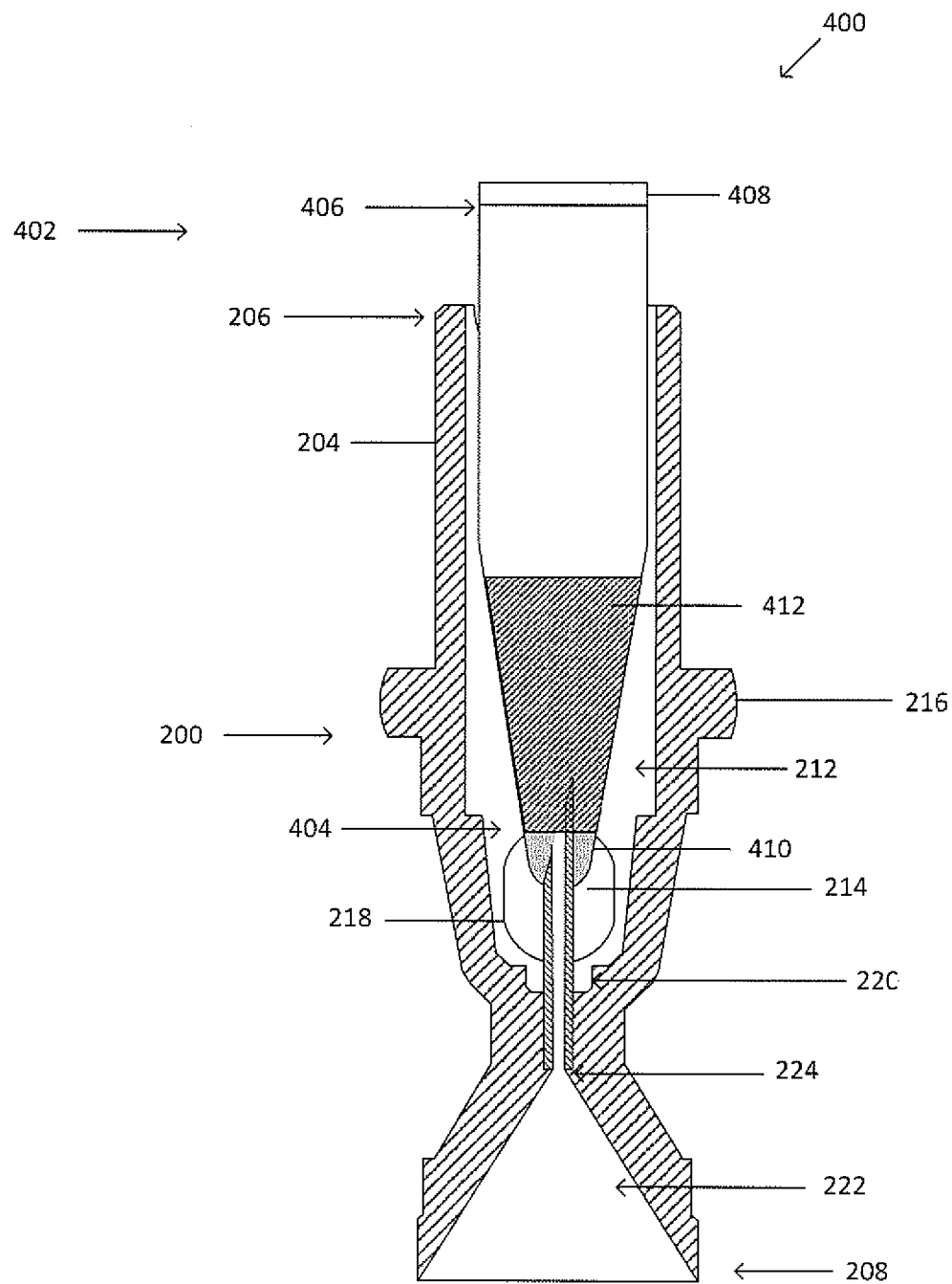

FIG. 4A shows an exploded view of the example collector 200 and processing vessel 402. FIG. 4B shows a cross-sectional view of the processing vessel 402 inserted into the cavity 212 at the first end 206 of the collector 200 taken along the line IV-IV shown in FIG. 4A. The collector 200 and processing vessel 402 form a collector-processing vessel system 400. The processing vessel 402 may be an Eppendorf tube, a syringe, or a test tube and has a closed end 404 and an open end 406. The open end 406 is sized to receive a cap 408. The cap 408 may be composed of re-sealable rubber or other suitable re-sealable material that can be repeatedly punctured with a needle or other sharp implement to access the contents stored in the processing vessel 402 interior and re-seals when the needle or implement is removed. Alternatively, the processing vessel 402 may also have two open ends that are sized to receive caps. The processing vessel 402 may have a tapered geometry that widens or narrows toward the open end 406; the processing vessel 402 may have a generally cylindrical geometry; or, the processing vessel 402 may have a generally cylindrical geometry in a first segment and a cone-shaped geometry in a second segment, where the first and second segments are connected and continuous with each other. Although at least one segment of the processing vessel 402 has a circular cross-section, in other embodiments, the at least one segment can have elliptical, square, triangular, rectangular, octagonal, or any other suitable cross-sectional shape. The processing vessel 402 can be composed of a transparent, semitransparent, opaque, or translucent material, such as plastic or another suitable material. The processing vessel includes a central axis 414, which when inserted into the cavity 212 is coaxial with the central axis 202 of the collector 200. The processing vessel 402 may also include a plug 410 at the closed end 404 to permit the introduction of the target material or to exchange or replace the target material with a collection fluid 412. The closed end 404 may be threaded to provide for a threaded connection with a threaded cavity 212 of the collector 200. The processing vessel 402 may be composed of glass, plastic, or other suitable material.

The plug 410 may be composed of re-sealable rubber or other suitable re-sealable material that can be repeatedly punctured with a needle or other sharp implement to access the contents of the processing vessel 402 interior or permit introduction of contents into the processing vessel 402 and re-seals when the needle or implement is removed. The plug 410 may be inserted into the processing vessel 402 such that a seal is maintained between the plug 410 and the processing vessel 402, such as by an interference fit. Alternatively, the plug 410 can be formed in the closed end 404 of the processing vessel 402 using heated liquid rubber that can be shaped while warm or hot and hardens as the rubber cools. An adhesive may be used to attach a plug 410 to the inner wall of the processing vessel can be a polymer-based adhesive, an epoxy, a contact adhesive or any other suitable material for bonding or creating a thermal bond. Alternatively, the plug 410 may be injected into the processing vessel 402. Alternatively, the plug 410 may be thermally bonded to the processing vessel 402.

In the example of FIG. 4B, the cannula 214 has a tapered tip that punctures the plug 410 and extends into an inner cavity of the processing vessel 402 with the shaft of the cannula 214 not extending into the inner cavity of the processing vessel 402. As explained in greater detail below, the inner cavity of the processing vessel 402 holds the target material. The cannula 214 may be covered by a resealable sleeve (not shown) to prevent the target material from flowing out unless the processing vessel 402 is in the cavity 212 to a depth that allows the cannula 214 to just penetrate the processing vessel 402. The resealable sleeve (not shown) covers the cannula 214, is spring-resilient, can be penetrated by the cannula 214, and is made of an elastomeric material capable of withstanding repeated punctures while still maintaining a seal.

As shown in FIGS. 4A-4B, the processing vessel 402 may be loaded with a collection fluid 412 prior to insertion into the collector 200. The collection fluid 412 displaces the target material, such that when the collector 200 and processing vessel 402 are inserted into the primary vessel (not shown) including the target material, and the collector, processing vessel, and primary vessel undergo centrifugation, the collection fluid 412 flows out of the processing vessel 402 and into the primary vessel, and, through displacement, such as through buoyant displacement (i.e. lifting a material upwards), pushes the target material through the cannula 214 and into the processing vessel 402.

The collection fluid 412 has a greater density than the density of the target material of the suspension (the density may be greater than the density of a subset of suspension fractions or all of the suspension fractions) and is inert with respect to the suspension materials. The collection fluid 412 may be miscible or immiscible in the suspension fluid. Examples of suitable collection fluids include, but are not limited to, solution of colloidal silica particles coated with polyvinylpyrrolidone (e.g. Percoll), polysaccharide solution (e.g. Ficoll), iodixanol (e.g. OptiPrep), an organic solvent, a liquid wax, an oil, a gas, and combinations thereof; olive oil, mineral oil, silicone oil, immersion oil, mineral oil, paraffin oil, silicon oil, fluorosilicone, perfluorodecalin, perfluoroperhydrophenanthrene, perfluorooctylbromide, and combinations thereof; organic solvents such as 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, and ionic liquids; polymer-based solutions; surfactants; perfluoroketones, such as perfluorocyclopentanone and perfluorocyclohexanone, fluorinated ketones, hydrofluoroethers, hydrofluorocarbons, perfluorocarbons, perfluoropolyethers, silicon and silicon-based liquids, such as phenylmethyl siloxane; and combinations thereof.

The processing vessel 402 may also include a processing solution (not shown) to effect a transformation on the target material when the target material enters the processing vessel 402. The processing solution (not shown) may be a preservative, a cell adhesion solution, a dye, or the like. Unlike the collection fluid 412, most, if not all, of the processing solution (not shown) remains within the processing vessel 402 upon centrifugation, thereby effecting the transformation on the target material in one manner or another (i.e. preserving, increasing adhesion properties, or the like). The processing solution (not shown) may be introduced as a liquid or as a liquid contained in a casing. The casing may be dissolvable in an aqueous solution but not in the collection fluid 412 (such as gel cap); or, the casing may be breakable, such that the casing breaks when the processing vessel 402 is shaken in a vortex mixer. Additionally, more than one processing solution may be used.

The processing vessel 402 may include a flexible cap that can be pushed to dispense a pre-determined volume therefrom and onto a substrate, such as a slide or a well plate. The cap 408 may be flexible or the cap 408 may be removed and the flexible cap inserted into the open end 406. Alternatively, the processing vessel 402 may be attached to (i.e. after accumulating the target material) or may include a dispenser, which is capable of dispensing a pre-determined volume of target material from the processing vessel 402 onto another substrate, such as a microscope slide. The dispenser may repeatedly puncture the re-sealable cap 408 or compress the material within the processing vessel 402 to withdraw and dispense the pre-determined volume of target material onto the substrate. Alternatively, the cap 408 may be removed and the dispenser (not shown) may be inserted directly into the processing vessel 402 to dispense the buffy coat-processing solution mixture.

Figure 4C:
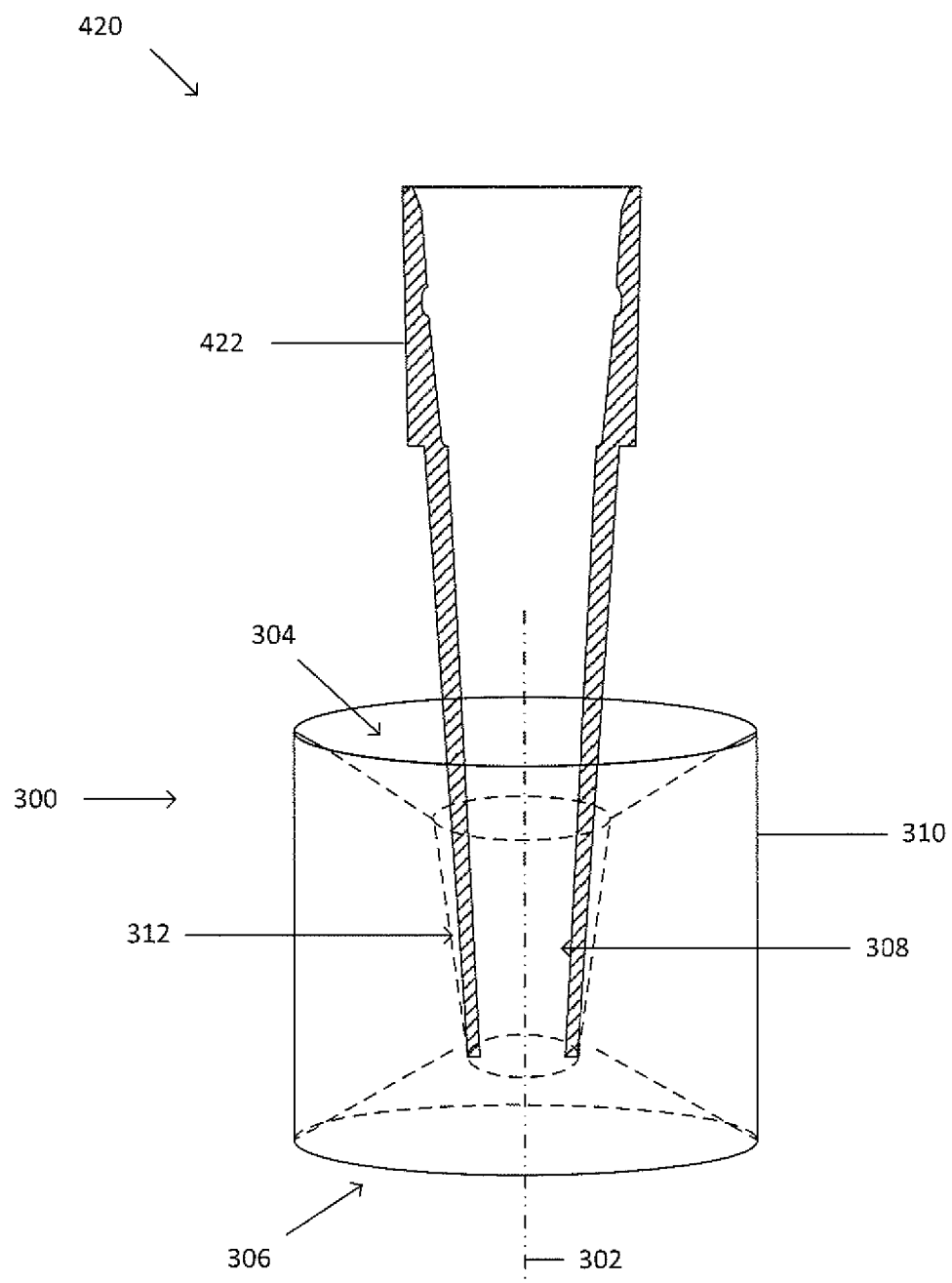
FIG. 4C shows an example collector-processing vessel system.

FIG. 4C shows an example collection system 420 including the collector 300 and a processing vessel 422. The processing vessel 422 is similar to the processing vessel 402. The processing vessel 422 may be inserted into the collector 300. The processing vessel 422 may receive the target material or the portion of the target material. Furthermore, the processing vessel 422 may be removed from the collector 300 and then placed into another vessel, such as a tube, an Eppendorf tube or a slide, to transfer the target material or the portion of the target material to the other vessel, such as by centrifugation, for further processing. Alternatively, an adapter, such as a ferrule, may be included to connect the processing vessel 422 to the collector 300. The adapter may be metal, plastic, glass, or the like.

Collector-Canopy System

Figure 5A:
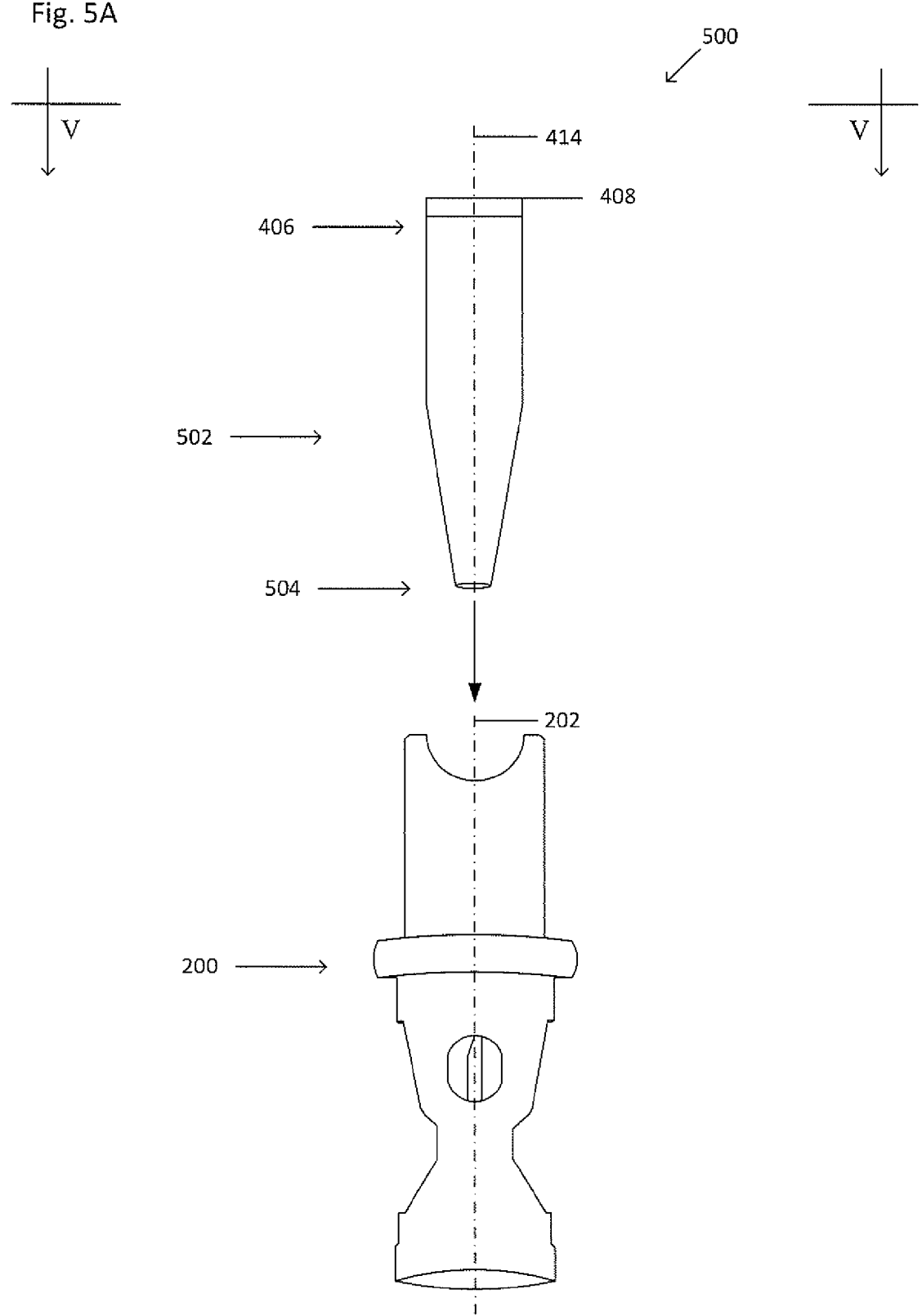
FIGS. 5A-5B show an example collector-canopy system.
Figure 5B:
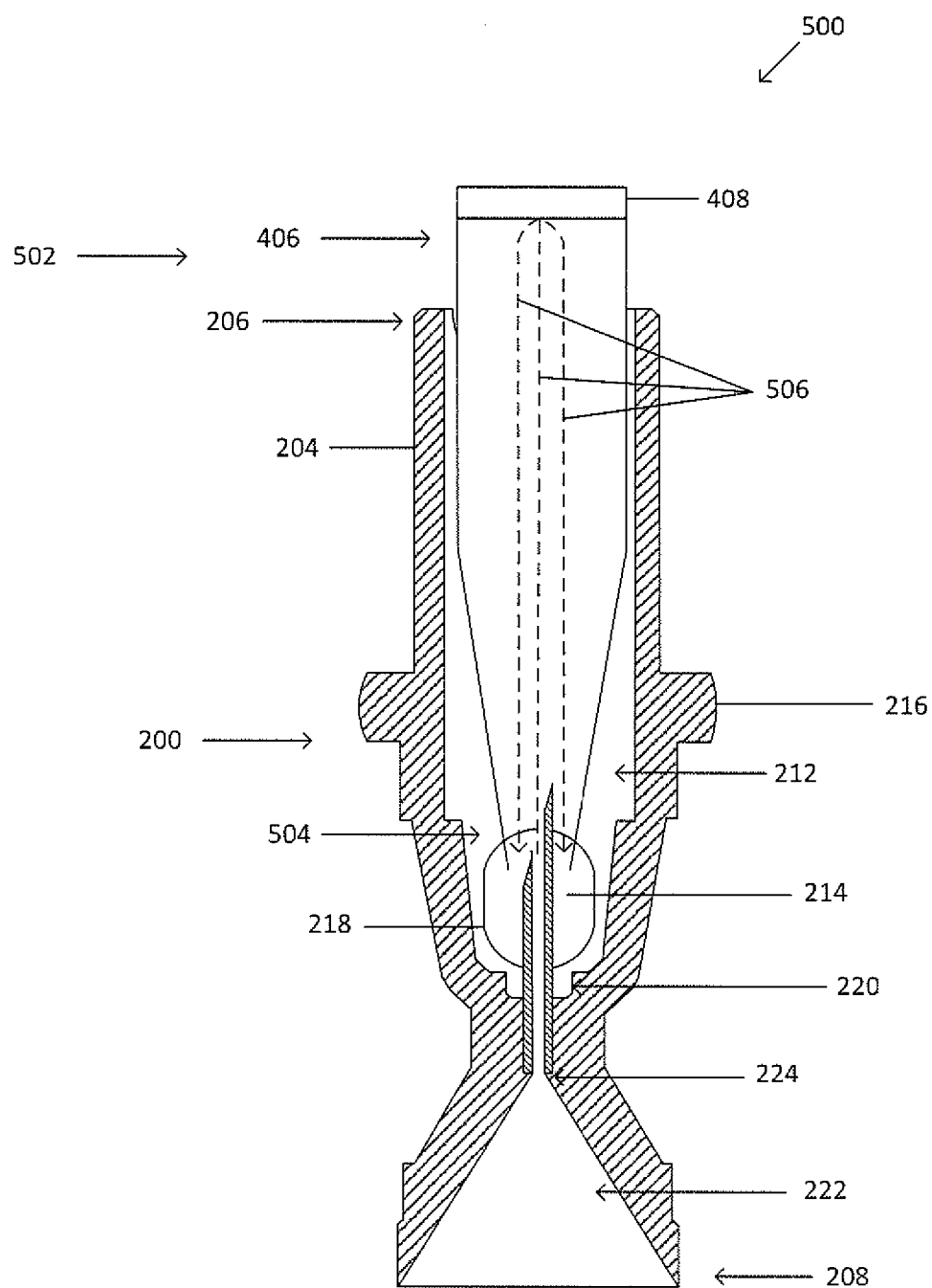

FIG. 5A shows an exploded view of the example collector 200 and canopy 502. FIG. 5B shows a cross-sectional view of the processing vessel 502 inserted into the cavity 212 of the collector 200 taken along the line V-V shown in FIG. 4A. The collector 200 and canopy 502 form a collector-canopy system 500. The canopy 502 is similar to the processing vessel 402, except that the canopy has a second open end 504. When the collector-canopy system 500 is inserted into the primary vessel, some fluid within the primary vessel, such as a portion of the suspension, a portion of a suspension fraction, a portion of a clearing fluid, or the like, may be discharged through the cannula 214. The canopy 502 inhibits a portion of the fluid in the primary vessel that may be discharged through the cannula 214 from escaping from the opening of the first end 206 of the collector 200. The discharged fluid, having been blocked by the canopy 502, flows out of the second open end 504, and out of the window 218. Dashed lines 506 show fluid flow as the fluid is discharged through the cannula 214 and retained by the canopy 502.

Alternatively, when the collector 230 is used, the lid 236 of the collector 230 inhibits a portion of the fluid in the primary vessel that may be discharged through the cannula 214 from escaping from the opening of the first end 206 of the collector 200 in a manner similar to that of the canopy 502.

Sealing Ring

Figure 6A:
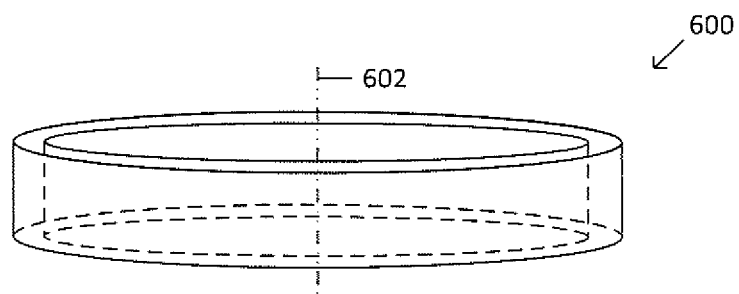
FIGS. 6A-6G show example sealing rings.
Figure 6B:
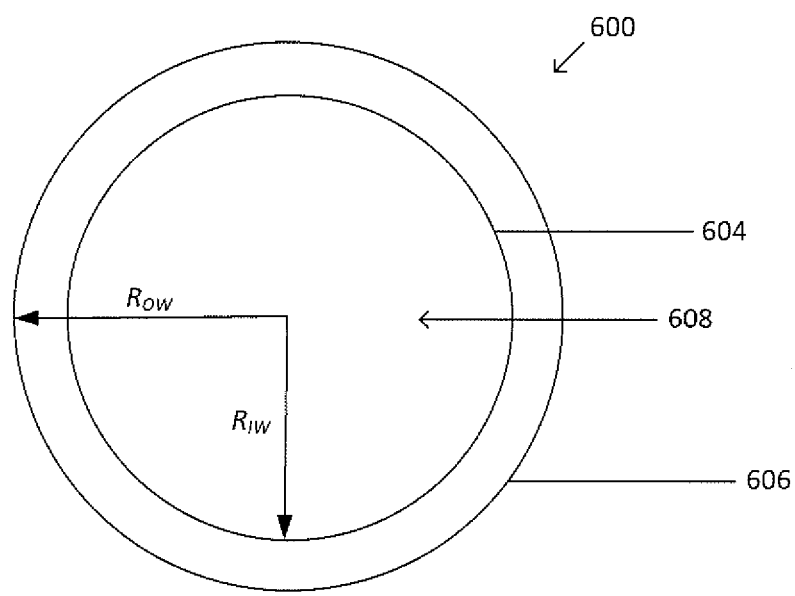

FIG. 6A shows an isometric view of a sealing ring 600. FIG. 6B shows a top down view of the sealing ring 600.

Dot-dashed line 602 represents the central or highest-symmetry axis of the sealing ring 600. The sealing ring 600 includes an inner wall 604, an outer wall 606, and a cavity 608. In FIG. 6B, $R_{IW}$ represents the radial distance from the center of the sealing ring 600 to the inner wall 604, and $R_{OW}$ represents the radial distance from the center of the sealing ring 600 to the outer wall 606. The sealing ring 600 is configured to fit around a primary vessel, such as a tube. The cavity 608 is sized and shaped to receive the primary vessel. The sealing ring 600 may be tightened, such that the size of the cavity 608 and the radii of the inner and outer walls 604 and 606 are reduced by circumferentially applying an approximately uniform, radial force, such as the radial force created by a clamp, around the outer wall 606 directed to the central axis 602 of the sealing ring 600. When the sealing ring 600 is tightened around the primary vessel, the uniform force applied to the sealing ring 600 is applied to the primary vessel, thereby causing the primary vessel to constrict. When the radial force is removed from the sealing ring 600, the sealing ring 600 remains tightened and in tension around the primary vessel.

Figure 6C:
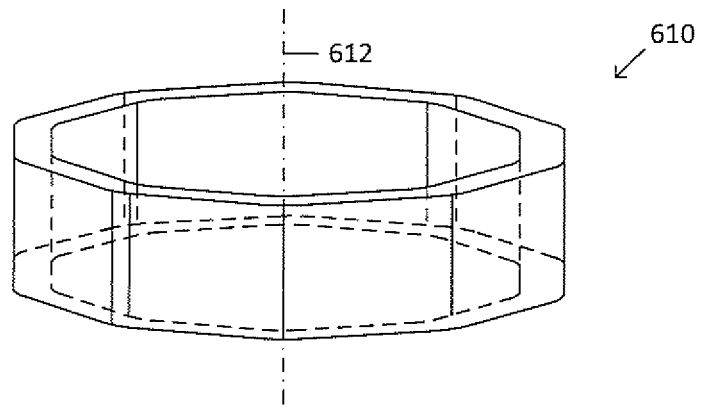
Figure 6D:
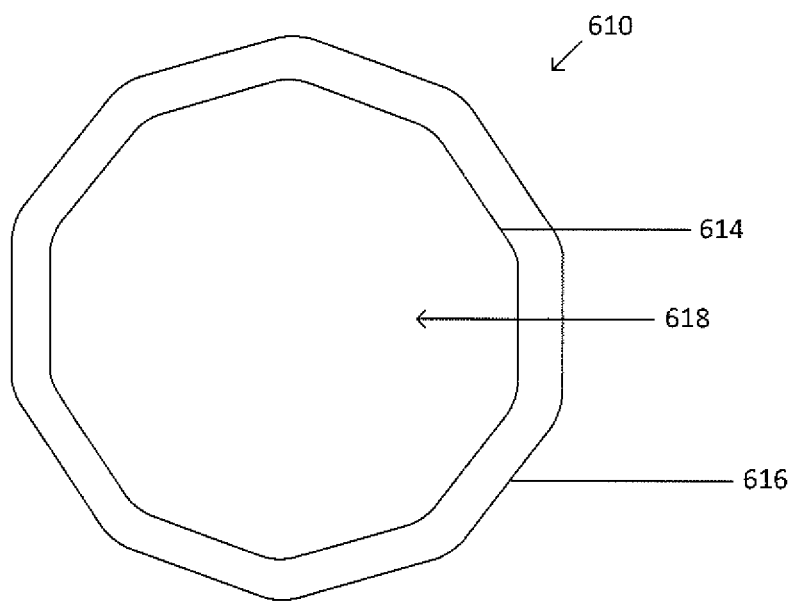

The sealing ring may be any shape, including, but not limited to, circular, triangular, or polyhedral. FIG. 6C shows an isometric view of a sealing ring 610. FIG. 6D shows a top down view of the sealing ring 610. Sealing ring 610 is similar to sealing ring 600, except sealing ring 610 is polyhedral. Dot-dashed line 612 represents the central or highest-symmetry axis of the sealing ring 610. The sealing ring 610 includes an inner wall 614, an outer wall 616, and a cavity 618. The sealing ring may be composed of a metal, such as brass, a polymer, or combinations thereof.

Figure 6E:
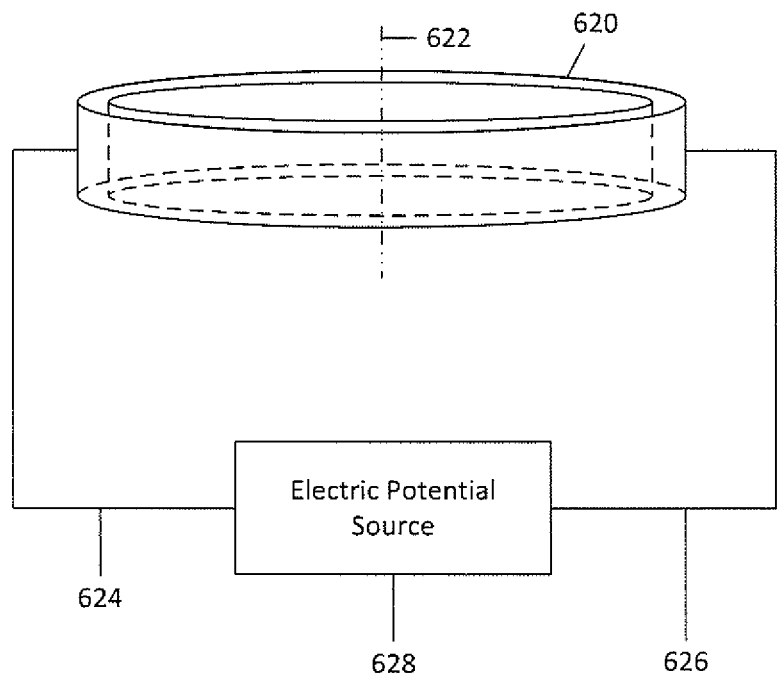
Figure 6F:
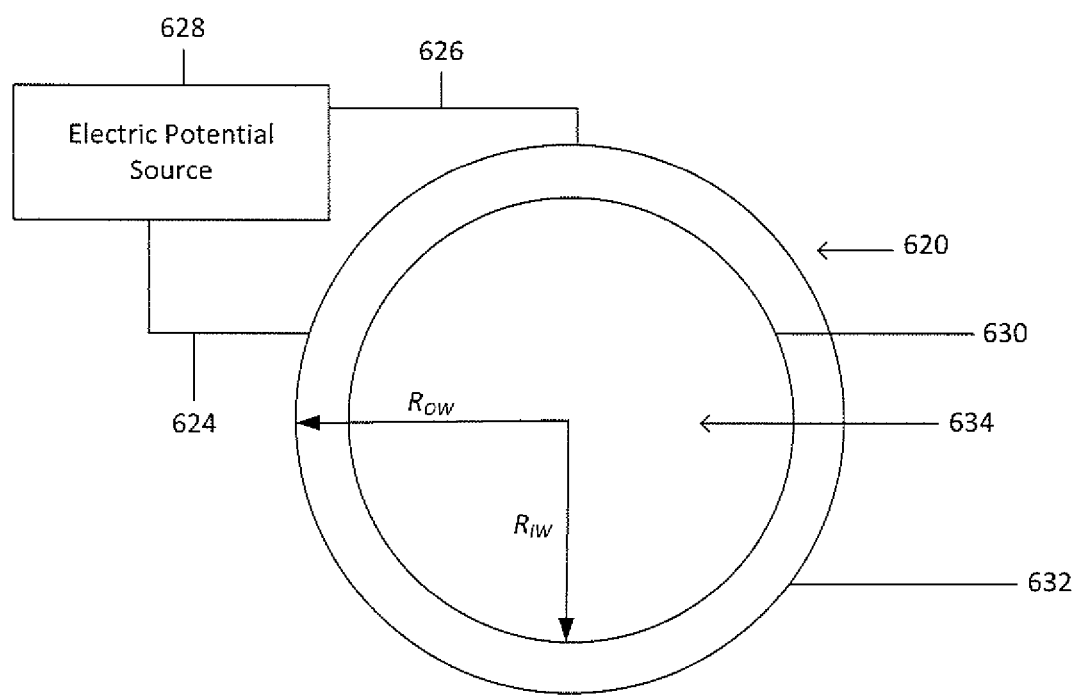

Alternatively, as shown in FIG. 6E, a sealing ring 620 may be composed of a piezoelectric material. FIG. 6F shows a top down view of the sealing ring 620. Dot-dashed line 622 represents the central or highest-symmetry axis of the sealing ring 620. The sealing ring 620 may be connected to an electric potential source 628, such as a battery, via a first lead 624 and a second lead 626. The electric potential source 628 creates a mechanical strain that causes the sealing ring 620 to tighten (i.e. sealing ring 620 radii decrease). The sealing ring 620 includes an inner wall 630, an outer wall 632, and a cavity 634. In FIG. 6F, $R_{IW}$ represents the radial distance from the center of the sealing ring 620 to the inner wall 630, and $R_{OW}$ represents the radial distance from the center of the sealing ring 620 to the outer wall 632. Alternatively, the sealing ring 620 may be in a naturally tightened stated. When applying the electric potential the sealing ring 620 expands. Alternatively, a portion of the sealing ring may be composed of the piezoelectric material, such that the piezoelectric portion acts as an actuator to cause the other portion of the sealing ring to tighten and apply the substantially uniform circumferential pressure on the primary vessel, thereby constricting the primary vessel to form the seal.

Figure 6G:
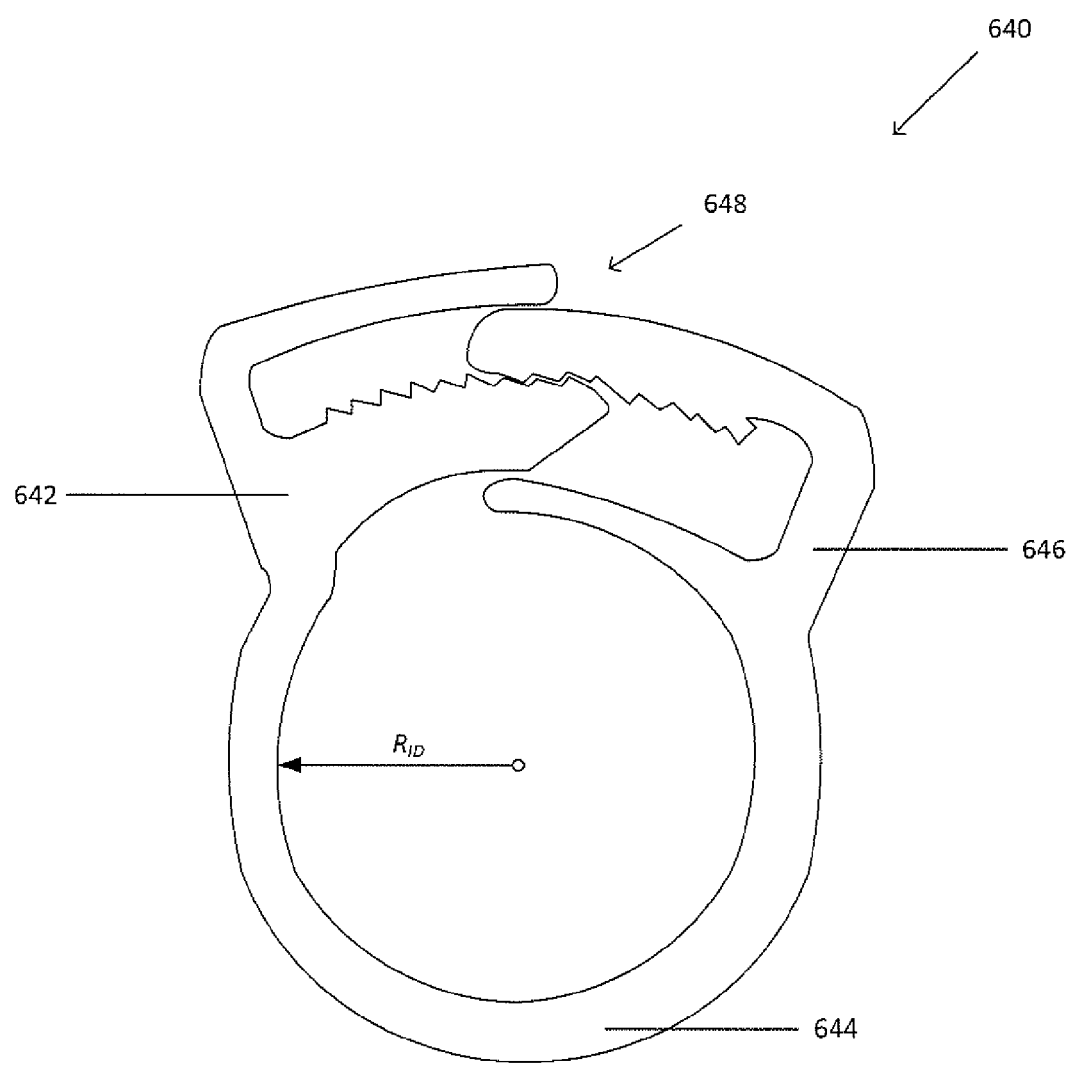

FIG. 6G shows an isometric view of a sealing ring 640. The sealing ring includes an adjustment mechanism 648 to adjust the inner diameter $R_{ID}$. The collapsible ring includes a processing vessel adapter 642 and a primary vessel adapter 646, the first and primary vessel adapters 642 and 646 being joined by a band portion 644. The first and primary vessel adapters 642 and 646 include complementary portions of the adjustment mechanism 648. The adjustment mechanism 648 includes, but is not limited to, a ratchet, tongue and groove, detents, or the like.

The sealing ring may also include a thermal element, such as a heated wire. The thermal element may soften the primary vessel for constriction. Alternatively, the thermal element may melt the primary vessel to provide a more adherent seal. Alternatively, the thermal element may cause the sealing ring to compress, thereby forming a seal between the primary vessel and float.

Sealing Ring

Figure 7:
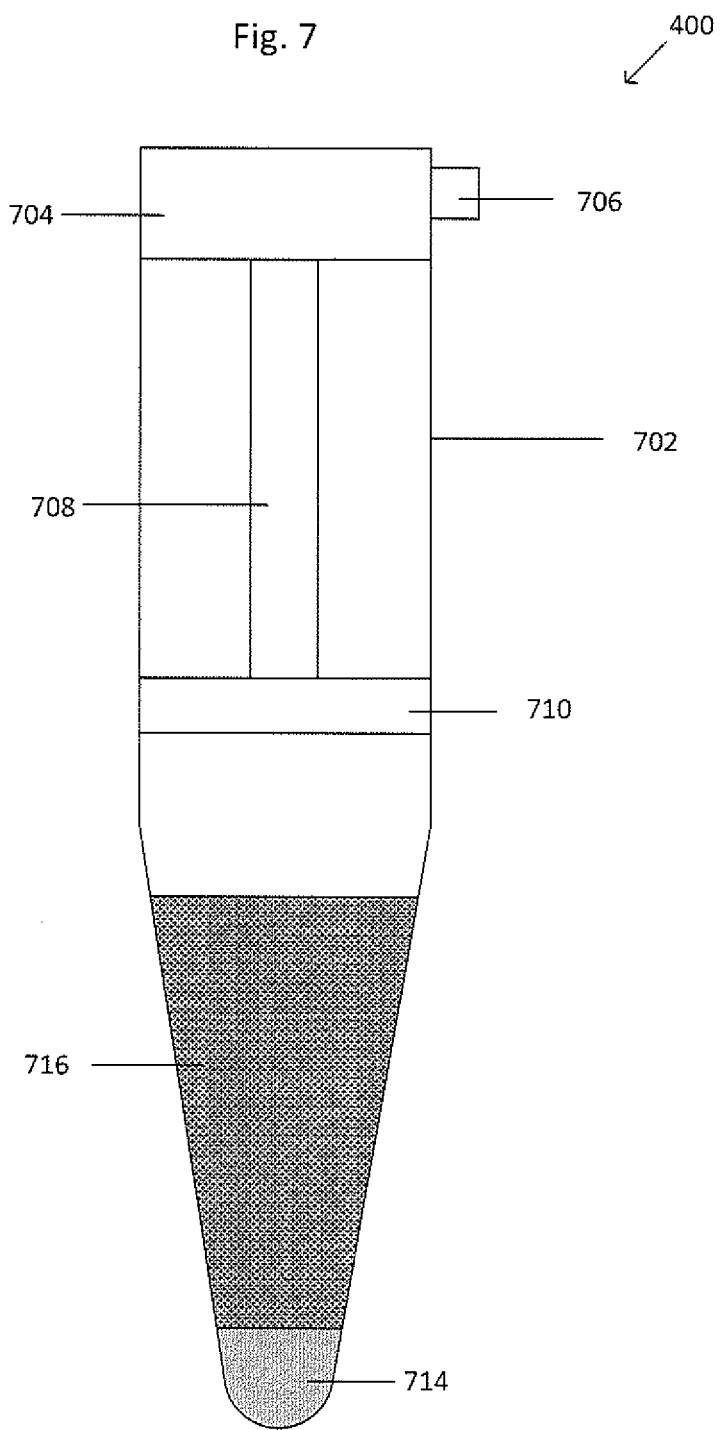
FIG. 7 shows an example fluid layering device.

FIG. 7 shows a fluid layering device 700. The fluid layering device 700 may include a motor 704 connected to a rod 708 which is also connected to a piston 710. The fluid layering device 700 may also include a switch 706 to activate or de-activate the motor 704. When the motor 704 is activated, the rod 708, which may be threaded, may rotate, thereby causing the piston 710 to move up and down, thereby creating a pressure gradient to expel a layering fluid 716 from the fluid layering device 700 a plug 714 when the fluid layering device 700 is inserted into the collector 200, such that the cannula 216 extends through the plug 714. Alternatively, the rod 708 may move up and down, thereby causing the piston 710 to move up and down, hence creating the pressure gradient. Alternatively, a cam mechanism, servomotor, diaphragm, or rack and pinion system may be used to either move the piston 710 up and down to create the pressure gradient or to create the pressure gradient without the piston 710.

The fluid layering device 700 may have a main body 702 with a tapered geometry that widens or narrows toward the plug 714; the fluid layering device 700 may have a generally cylindrical geometry; or, the fluid layering device 700 may have a generally cylindrical geometry in a first segment and a cone-shaped geometry in a second segment, where the first and second segments are connected and continuous with each other. Although at least one segment of the fluid layering device 700 has a circular cross-section, in other embodiments, the at least one segment can have elliptical, square, triangular, rectangular, octagonal, or any other suitable cross-sectional shape. The fluid layering device 700 can be composed of a transparent, semitransparent, opaque, or translucent material, such as plastic or another suitable material. The processing vessel includes a central axis, which when inserted into the cavity 212 of the collector 200 is coaxial with the central axis 202 of the collector 200. The plug 714 permits the introduction of the layering fluid 716 into the primary vessel via the cannula 216 of the collector 200.

The plug 714 may be composed of re-sealable rubber or other suitable re-sealable material that can be repeatedly punctured with a needle or other sharp implement to access the contents of the fluid layering device 700 interior or permit introduction of contents into the fluid layering device 700 and re-seals when the needle or implement is removed. The plug 714 may be inserted into the fluid layering device 700 such that a seal is maintained between the plug 714 and the fluid layering device 700, such as by an interference fit. Alternatively, the plug 714 can be formed in the closed end 404 of the fluid layering device 700 using heated liquid rubber that can be shaped while warm or hot and hardens as the rubber cools. An adhesive may be used to attach a plug 714 to the inner wall of the processing vessel can be a polymer-based adhesive, an epoxy, a contact adhesive or any other suitable material for bonding or creating a thermal bond. Alternatively, the plug 714 may be injected into the fluid layering device 700. Alternatively, the plug 714 may be thermally bonded to the fluid layering device 700.

The fluid layering device 700 may also include a controller (not shown) to control the output of the motor 704, such as the frequency and/or amplitude of the various strokes.

The fluid layering device 700 may also include a battery (not shown) which may be chargeable or replaceable.

The layering fluid 716 may be miscible or immiscible with the suspension fluid and inert with respect to the suspension materials. Examples of suitable layering fluids include, but are not limited to, solution of colloidal silica particles coated with polyvinylpyrrolidone (e.g. Percoll), polysaccharide solution (e.g. Ficoll), iodixanol (e.g. OptiPrep), an organic solvent, a liquid wax, an oil, a gas, and combinations thereof; olive oil, mineral oil, silicone oil, immersion oil, mineral oil, paraffin oil, silicon oil, fluorosilicone, perfluorodecalin, perfluoroperhydrophenanthrene, perfluorooctylbromide, and combinations thereof; organic solvents such as 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, and ionic liquids; polymer-based solutions; surfactants; perfluoroketones, such as perfluorocyclopentanone and perfluorocyclohexanone, fluorinated ketones, hydrofluoroethers, hydrofluorocarbons, perfluorocarbons, perfluoropolyethers, silicon and silicon-based liquids, such as phenylmethyl siloxane; and combinations thereof.

Methods

For the sake of convenience, the methods are described with reference to an example suspension of anticoagulated whole blood. But the methods described below are not intended to be so limited in their scope of application. The methods, in practice, may be used with any kind of sample, such as a suspension or other biological fluid. For example, a sample may be urine, blood, bone marrow, cystic fluid, ascites fluid, stool, semen, cerebrospinal fluid, synovial fluid, nipple aspirate fluid, saliva, amniotic fluid, vaginal secretions, mucus membrane secretions, aqueous humor, vitreous humor, vomit, a suspension derived from a tissue sample or a culture sample, and any other physiological fluid or semi-solid. It should also be understood that a target material may be a fraction of a sample or a sub-fraction of a fraction, such as a portion of buffy coat. The target material may include an analyte, such as a cell, such as ova, a nucleated red blood cell, or a circulating tumor cell ("CTC"), a circulating endothelial cell, a fetal cell, a vesicle, a liposome, a protein, a nucleic acid, a biological molecule, a naturally occurring or artificially prepared microscopic unit having an enclosed membrane, a parasite (e.g. spirochetes, such as *Borrelia burgdorferi*), a microorganism, a virus, or an inflammatory cell; or, the target material may be the analytes.

Figure 8:
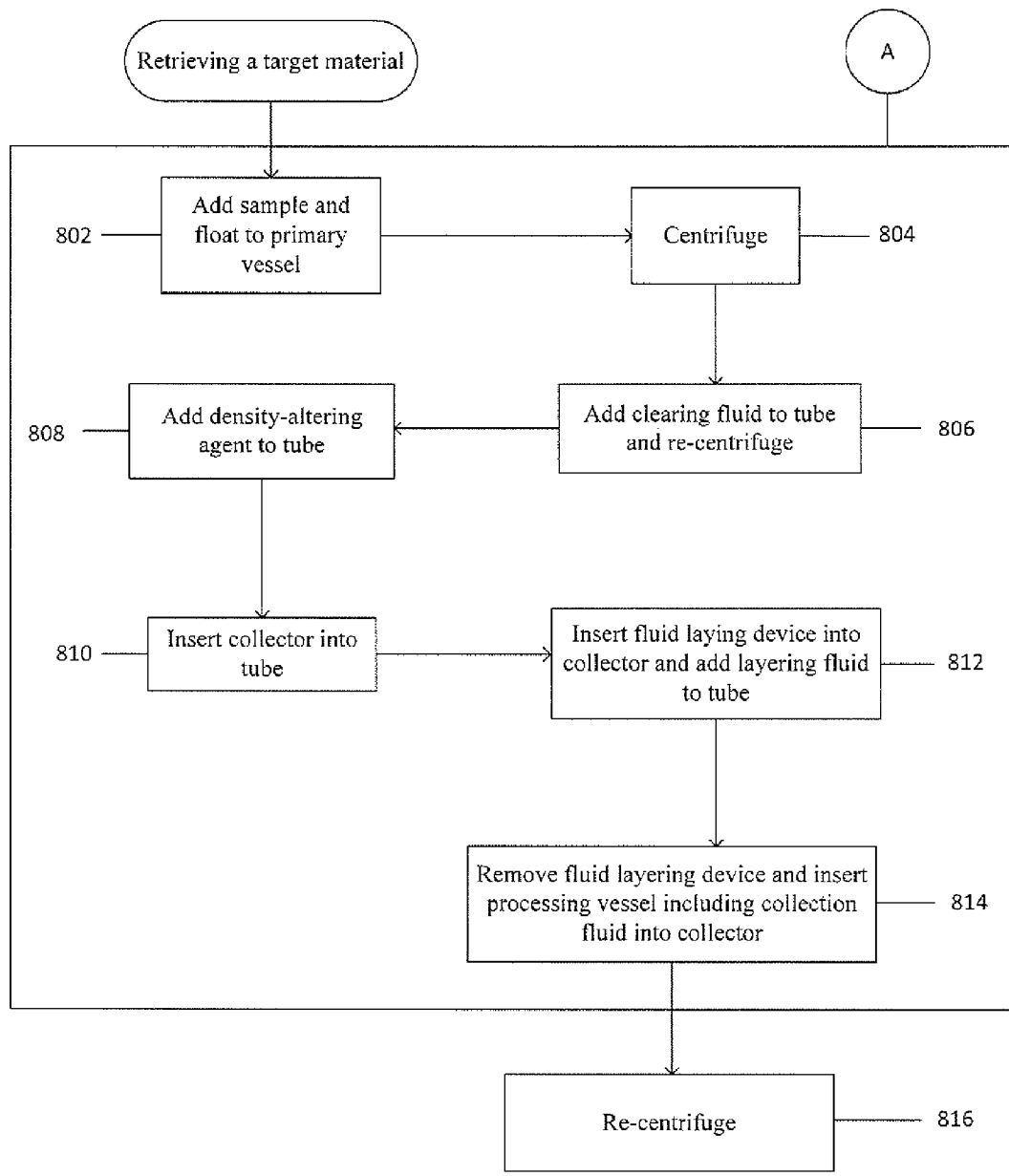
FIG. 8 shows a flow diagram of an example method for retrieving a target material.

FIG. 8 shows a flow diagram for an example method for retrieving a target material. In block 802, a sample, such as anticoagulated whole blood, is obtained, and is added to a primary vessel, such as a test tube. A float may also be added to the primary vessel. For the sake of convenience, the methods are described with reference to the float, but the methods described below are not intended to be so limited in their application and may be performed without the float.

A depletion reagent may be added to the sample to remove non-target material, such as by lysing the non-target material or changing the density of the non-target material. Examples of suitable depletion reagents include, but are not limited to, solution of colloidal silica particles coated with polyvinylpyrrolidone (e.g. Percoll), polysaccharide solution (e.g. Ficoll), iodixanol (e.g. OptiPrep), a complex, branch glucan (e.g. Dextran), cesium chloride, sucrose, sugar-based solutions, polymer solutions, multi-phase polymer solutions, tetrameric antibody complexes (e.g. RosetteSep) or the like.

FIG. 9A shows an isometric view of an example primary vessel and float system 900. The system 900 includes a primary vessel 902 and a float 904 suspended within whole blood 906. In the example of FIG. 9A, the primary vessel 902 has a circular cross-section, a first open end 910, and a second closed end 908. The open end 910 is sized to receive a cap 912. The primary vessel may also have two open ends that are sized to receive caps, such as the example tube and separable float system 920 shown FIG. 9B. The system 920 is similar to the system 900 except the primary vessel 902 is replaced by a primary vessel 922 that includes two open ends 924 and 926 configured to receive the cap 912 and a cap 928, respectively. The primary vessels 902 and 922 have a generally cylindrical geometry, but may also have a tapered geometry that widens, narrows, or a combination thereof toward the open ends 910 and 924, respectively. Although the primary vessels 902 and 922 have a circular cross-section, in other embodiments, the primary vessels 902 and 922 can have elliptical, square, triangular, rectangular, octagonal, or any other suitable cross-sectional shape that substantially extends the length of the tube. The primary vessels 902 and 922 can be composed of a transparent, semitransparent, opaque, or translucent material, such as plastic or another suitable material. The primary vessels 902 and 922 each include a central axis 918 and 930, respectively. The primary vessel 902 may also include a septum 914, as seen in magnified view 916, at the closed end 908 to permit the removal of a fluid, the suspension, or a suspension fraction, whether with a syringe, a pump, by draining, or the like. The primary vessel 902 may have an inner wall and a first diameter.

The septum 914 may be composed of re-sealable rubber or other suitable re-sealable material that can be repeatedly punctured with a needle or other sharp implement to access the contents of the primary vessel 902 interior and re-seals when the needle or implement is removed. The septum 914 may be inserted into the primary vessel 902 such that a seal is maintained between the septum 914 and the primary vessel 902, such as by an interference fit. Alternatively, the septum 914 can be formed in the openings and/or the bottom interior of the tube using heated liquid rubber that can be shaped while warm or hot and hardens as the rubber cools. An adhesive may be used to attach the septum 914 to the wall of the opening and tube interior and can be a polymer-based adhesive, an epoxy, a contact adhesive or any other suitable material for bonding rubber to plastic or creating a thermal bond. Alternatively, the septum 914 may be thermally bonded to the primary vessel 902.

The float 904 includes a main body, two teardrop-shaped end caps, and support members radially spaced and axially oriented on the main body. Alternatively, the float 904 may not include any support members. Alternatively, the float 904 may include support members which do not engage the inner wall of the primary vessel 902.

In alternative embodiments, the number of support members, support member spacing, and support member thickness can each be independently varied. The support members can also be broken or segmented. The main body is sized to have an outer diameter that is less than the inner diameter of the primary vessel 902, thereby defining fluid retention channels between the outer surface of the main body and the inner wall of the primary vessel 902. The surfaces of the main body between the support members can be flat, curved or have another suitable geometry. The support members and the main body may be a singular structure or may be separate structures.

Embodiments include other types of geometric shapes for float end caps. The top end cap may be teardrop-shaped, dome-shaped, cone-shaped, or any other appropriate shape. The bottom end cap may be teardrop-shaped, dome-shaped, cone-shaped, or any other appropriate shape. In other embodiments, the main body of the float 904 can include a variety of different support structures for separating samples, supporting the tube wall, or directing the suspension fluid around the float during centrifugation. Embodiments are not intended to be limited to these examples. The main body may include a number of protrusions that provide support for the tube. In alternative embodiments, the number and pattern of protrusions can be varied. The main body may include a single continuous helical structure or shoulder that spirals around the main body creating a helical channel. In other embodiments, the helical shoulder can be rounded or broken or segmented to allow fluid to flow between adjacent turns of the helical shoulder. In various embodiments, the helical shoulder spacing and rib thickness can be independently varied. In another embodiment, the main body may include a support member extending radially from and circumferentially around the main body. In another embodiment, the support members may be tapered.

The float 904 can be composed of a variety of different materials including, but not limited to, metals; organic or inorganic materials; ferrous plastics; sintered metal; machined metal; plastic materials and combinations thereof. The primary vessel 902 may have an inner wall and a first diameter. The float 904 can be captured within the primary vessel 902 by an interference fit, such that under centrifugation, an inner wall of the tube expands to permit axial movement of the float 904. When centrifugation stops, the inner wall reduces back to the first diameter to induce the interference fit. Alternatively, the inner wall may not expand and the interference fit may not occur between the float 904 and the primary vessel 902, such that the float moves freely within the tube before, during, or after centrifugation. The end caps of the float may be manufactured as a portion of the main body, thereby being one singular structure, by machining, injection molding, additive techniques, or the like; or, the end caps may be connected to the main body by a press fit, an adhesive, a screw, any other appropriate method by which to hold at least two pieces together, or combinations thereof.

The cap 912 may be composed of a variety of different materials including, but not limited to, organic or inorganic materials; plastic materials; and combination thereof.

In block 804, the sample, the float, and the primary vessel undergo centrifugation. FIG. 10 shows an isometric view of the primary vessel and float system 900 having undergone density-based separation, such as by centrifugation. Suppose, for example, the centrifuged whole blood includes three fractions. For convenience sake, the three fractions include plasma, buffy coat, and red blood cells. However, when another suspension undergoes centrifugation, there may be more than, less than, or the same number of fractions, each fraction having a different density. The suspension undergoes axial separation into three fractions along the length the tube based on density, with red blood cells 1003 located on the bottom, plasma 1001 located on top, and buffy coat 1002 located in between, as shown in FIG. 10. The float 904 may have any appropriate density to settle within one of the fractions. The density of the float 904 can be selected so that the float 904 expands the buffy coat 1002 between the main body of the float and the inner wall of the primary vessel. The buffy coat 1002 can be trapped within an area between the float 904 and the primary vessel 902.

Figure 11A:
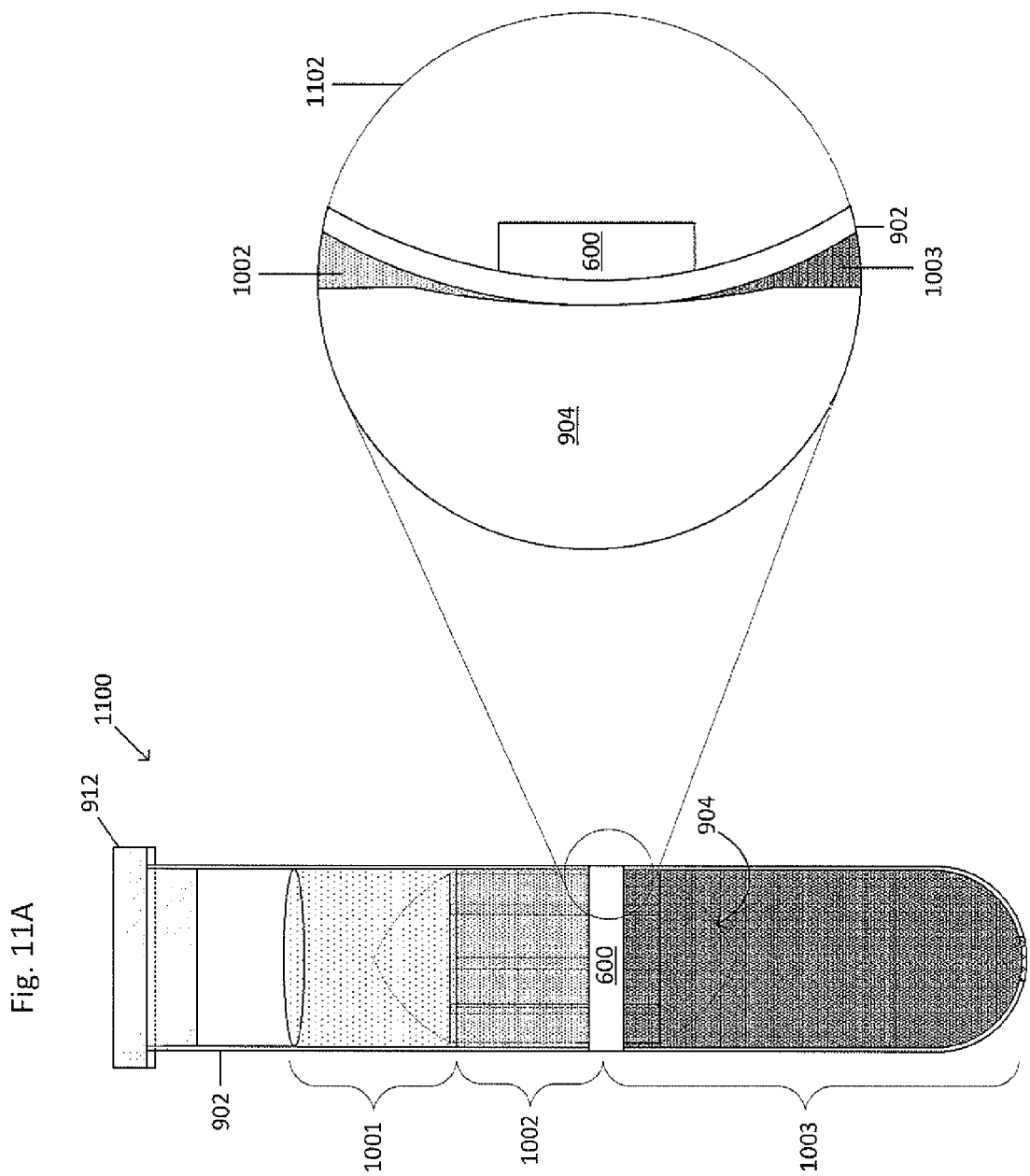

FIGS. 11A and 11B show a first seal being formed to prevent fluids from moving up or down within the primary vessel. For convenience, FIG. 11A shall be used to describe the method, though the method applies equally to FIG. 11B. The first seal also inhibits float movement. The first sealing ring 600 may be placed at approximately a lower end of the main body of the float 904. The first sealing ring 600 exerts circumferential or radial forces on the primary vessel 902, thereby causing the primary vessel 902 to collapse inwardly against the float 904. Magnified view 1102 shows the first sealing ring 600 tightened around the float and primary vessel system 900. The first sealing ring 600, having been placed at an interface of the buffy coat 1002 and the red blood cells 1003, causes the primary vessel 902 to collapse inwardly until a seal is formed between the primary vessel 902 and the float 904. An outer wall of the first sealing ring 600 may sit flush with an outer wall of the primary vessel 902; the outer wall of the first sealing ring 600 may extend past the outer wall of the primary vessel 902; or, the outer wall of the primary vessel 902 may extend past the outer wall of the first sealing ring 600. The first sealing ring 600 remains tightened to maintain the seal, which prevents fluids from moving past the seal in any direction. The first sealing ring 600 may also remain in tension. Alternatively, the first sealing ring 600 may be overtightened and then the force applied to the first sealing ring 600 is removed. The first sealing ring 600 may expand slightly, though still remains constricted.

To apply the first sealing ring 600 and thereby form the seal, a clamp may be used to circumferentially apply a force directed toward the central axis of the primary vessel 902 to the first sealing ring 600 and the float and primary vessel system 900. The first sealing ring 600 is placed around the float and primary vessel system 900 after the float and primary vessel system 900 have undergone density-based separation, such as by centrifugation. The first sealing ring 600 and float and primary vessel system 900 are then placed into the clamp. The clamp may include a shelf to support the first sealing ring 600 against the primary vessel 902. Operation of the clamp may be automated or may be performed manually. Alternatively, the clamp may form a seal between the float 904 and primary vessel 902 without the inclusion of the first sealing ring 600. Alternatively, a seal may be formed between the float 904 and the primary vessel 902 such as by ultrasonic welding; or by applying heat or a temperature gradient to deform and/or melt the primary vessel 902 to the float 904. For the sake of convenience, the methods are described with reference to the seal between the float and the primary vessel, but the methods described below are not intended to be so limited in their application and may be performed without the seal.

When operation of the clamp is automated, a motor causes translation of either a collet, including collet fingers, or a pressure member to cause compression of the collet fingers. The motor may be connected to the collet or the pressure member by a shaft, such as a cam shaft, and one or more gears. A base engages and holds the object. When the collet is driven by the motor, the pressure member remains stationary. When the pressure member is driven by the motor, the collet remains stationary. The clamp may include a release, so as to cause the pressure member to slide off of the collet fingers 904, thereby removing the clamping force.

Alternatively, the clamp may be, but is not limited to, a collet clamp, an O-ring, a pipe clamp, a hose clamp, a spring clamp, a strap clamp, or a tie, such as a zip tie. The clamp may be used without a first sealing ring to provide a seal between a float and a tube.

Figure 12A:
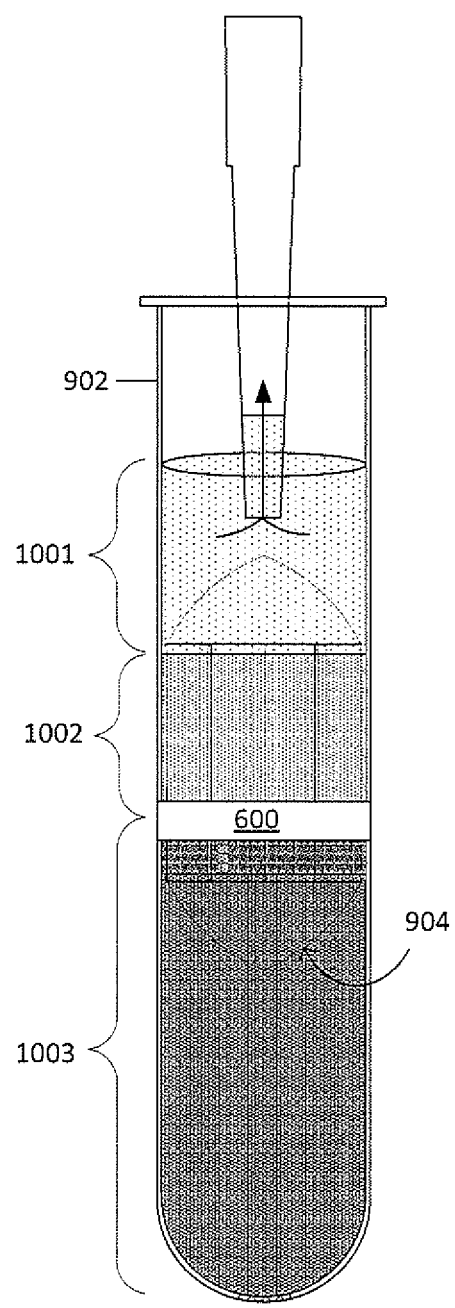
FIGS. 12A-12G show an example system retrieving a target material.
Figure 12C:
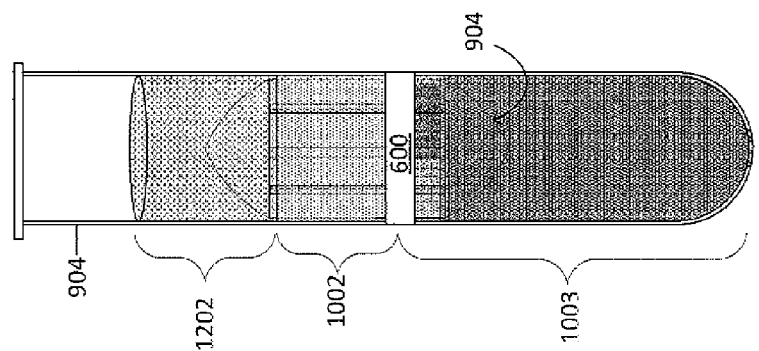
Figure 12B:
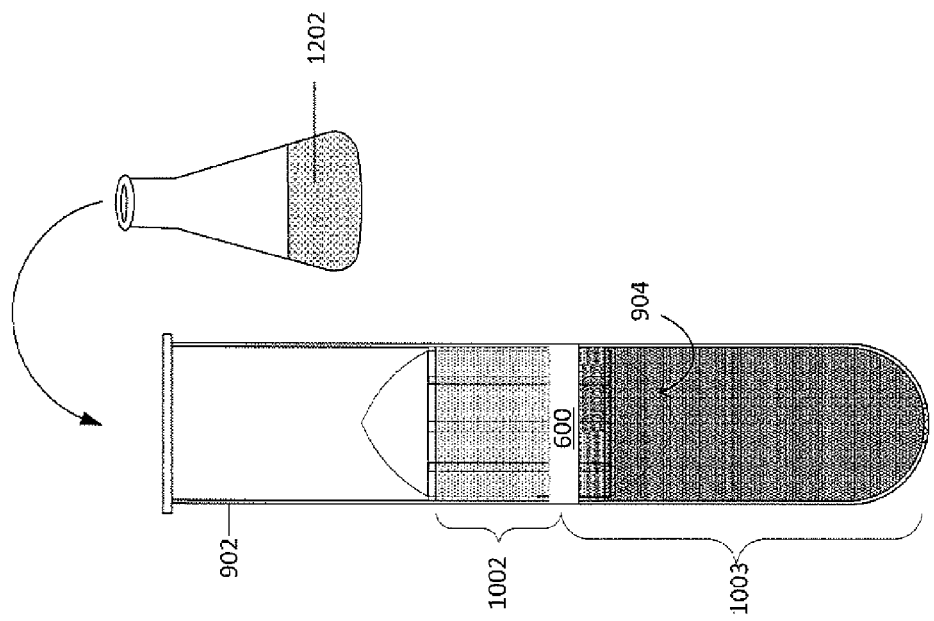

The plasma 1001 may be removed from the primary vessel 902, as shown in FIG. 12A, such as by pipetting, suctioning, pouring, or the like. Returning to FIG. 8, in block 806, a clearing fluid 1202 may be added to the primary vessel 902 and the system undergoes centrifugation again, as shown in FIGS. 12B-12C. The clearing fluid 1202 has a density greater than the buffy coat 1002, but may be layered on top of the buffy coat 1002. It may be desirous to gently layer the clearing fluid 1202 on top of the buffy coat 1002 to inhibit mixing of the clearing fluid 1202 with the buffy coat 1002. During centrifugation, the clearing fluid 1202 moves underneath the buffy coat 1002 but remains above the clamp 600. After centrifugation, the buffy coat 1002, having a density less than the clearing fluid 1202, rests on top of the clearing fluid 1202. An appropriate amount of the clearing fluid 1202, such as up to 500 milliliters, may be added to the primary vessel 902, such that the buffy coat 1002 is not between the main body of the float 904 and the inner wall of the primary vessel 902. The clearing fluid 1202 may be miscible or immiscible with the suspension fluid and inert with respect to the suspension materials. Examples of suitable clearing fluids include, but are not limited to, solution of colloidal silica particles coated with polyvinylpyrrolidone (e.g. Percoll), polysaccharide solution (e.g. Ficoll), iodixanol (e.g. OptiPrep), an organic solvent, a liquid wax, an oil, a gas, and combinations thereof; olive oil, mineral oil, silicone oil, immersion oil, mineral oil, paraffin oil, silicon oil, fluorosilicone, perfluorodecalin, perfluoroperhydrophenanthrene, perfluorooctylbromide, and combinations thereof; organic solvents such as 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, and ionic liquids; polymer-based solutions; surfactants; perfluoroketones, such as perfluorocyclopentanone and perfluorocyclohexanone, fluorinated ketones, hydrofluoroethers, hydrofluorocarbons, perfluorocarbons, perfluoropolyethers, silicon and silicon-based liquids, such as phenylmethyl siloxane; and combinations thereof.

Figure 12D:
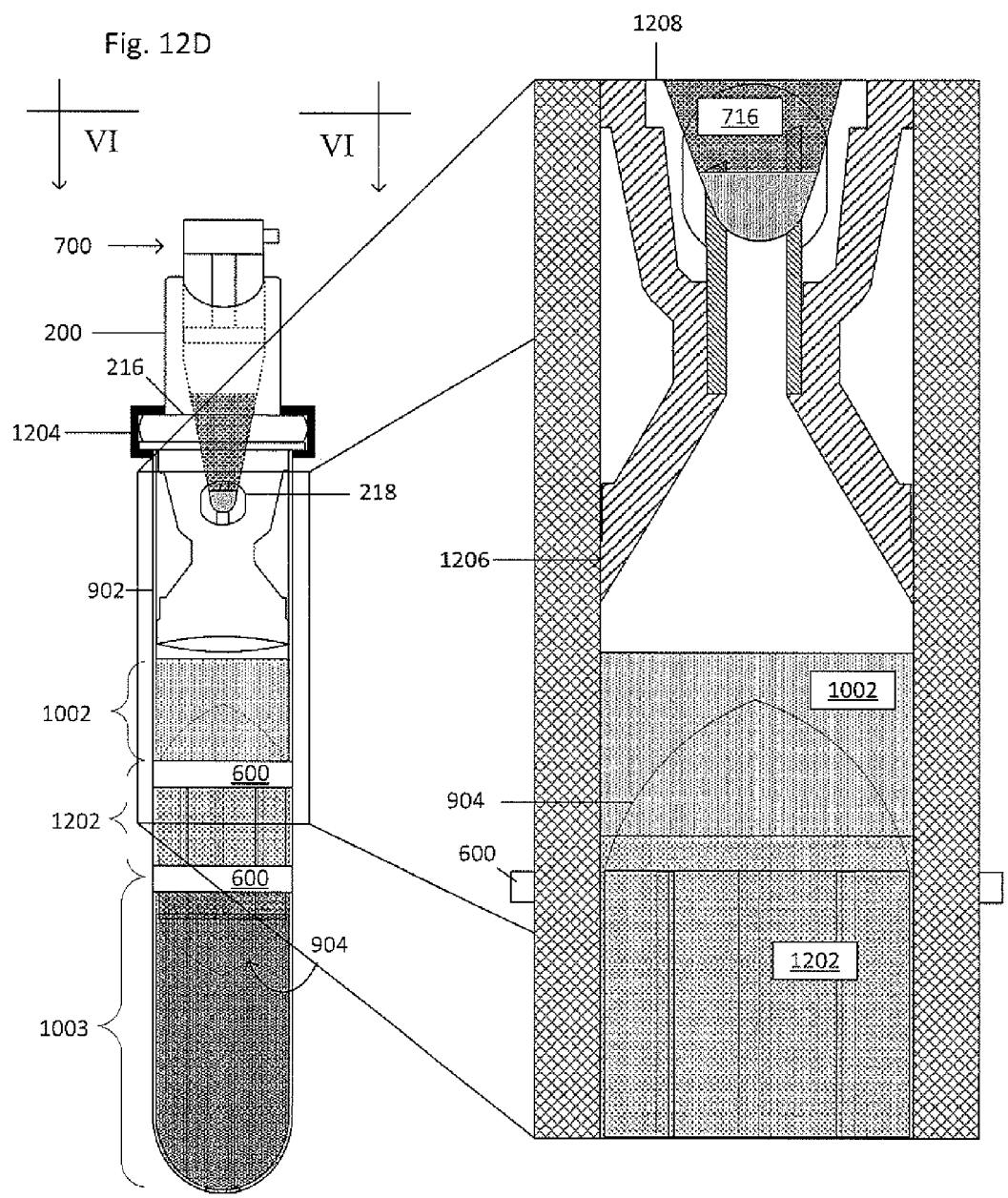

A second sealing ring 600 may be placed at approximately an upper end of the main body of the float 904, as shown in FIG. 12D. Returning to FIG. 8, in block 808, a density-altering agent may be added to the primary vessel 902 to change the density of non-target material relative to the density the of target material. For example, the target material may be circulating tumor cells or fetal cells. The density-altering agent may be added to change the density of the fluid within which these cells float without changing the density of the cells. The density of the fluid and any additional non-target materials may be made greater than the density of the target material, such as the cells. Examples of suitable fraction-changing-density solutions include, but are not limited to, solution of colloidal silica particles coated with polyvinylpyrrolidone (e.g. Percoll), polysaccharide solution (e.g. Ficoll), iodixanol (e.g. OptiPrep), a complex, branch glucan (e.g. Dextran), cesium chloride, sucrose, sugar-based solutions, polymer solutions, multi-phase polymer solutions, tetrameric antibody complexes (e.g. RosetteSep) or the like.

To be imaged, a solution containing a fluorescent probe may be used to label the target material, thereby providing a fluorescent signal for identification and characterization, such as through imaging. The fluorescent probe may be added to the primary vessel after the second sealing ring has been applied or after at least one non-target material, such as the plasma, has been removed. The solution containing the fluorescent probe may be added to the suspension before the suspension is added to the vessel, after the suspension is added to the vessel but before centrifugation, or after the suspension has undergone centrifugation. The fluorescent probe includes a fluorescent molecule bound to a ligand. The target material may have a number of different types of surface markers. Each type of surface marker is a molecule, such an antigen, capable of attaching a particular ligand, such as an antibody. As a result, ligands may be used to classify the target material and determine the specific type of target materials present in the suspension by conjugating ligands that attach to particular surface markers with a particular fluorescent molecule. Examples of suitable fluorescent molecules include, but are not limited to, quantum dots; commercially available dyes, such as fluorescein, Hoechst, FITC ("fluorescein isothiocyanate"), R-phycoerythrin ("PE"), Texas Red, allophycocyanin, Cy5, Cy7, cascade blue, DAPI ("4',6-diamidino-2-phenylindole") and TRITC ("tetramethylrhodamine isothiocyanate"); combinations of dyes, such as CY5PE, CY7APC, and CY7PE; and synthesized molecules, such as self-assembling nucleic acid structures. Many solutions may be used, such that each solution includes a different type of fluorescent molecule bound to a different ligand.

In block 810, a collector, such as the collector 200, may be inserted into the primary vessel 902. In block 812, a fluid layering device 700 may be inserted into the collector 200. FIG. 12D shows the collector 200 inserted into the primary vessel 902 and also forming a seal 1206 between the second end 208 of the collector 200 and the inner wall of the primary vessel 902. The layering fluid 716 may be added to the primary vessel 902 by the fluid layering device 700 via the cannula 216 of the collector 200, as shown in FIG. 12E.

Figure 12E:
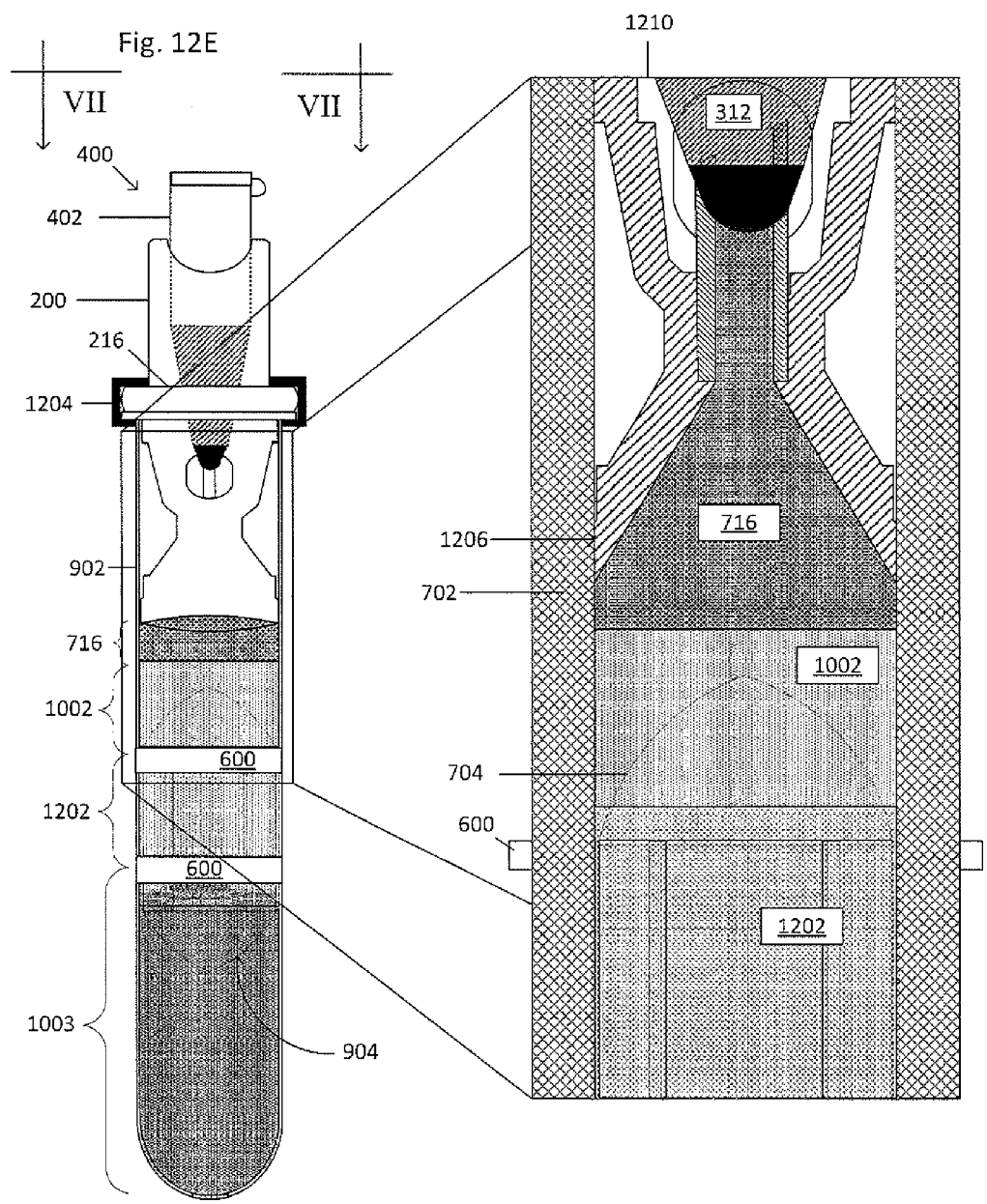
Figure 12F:
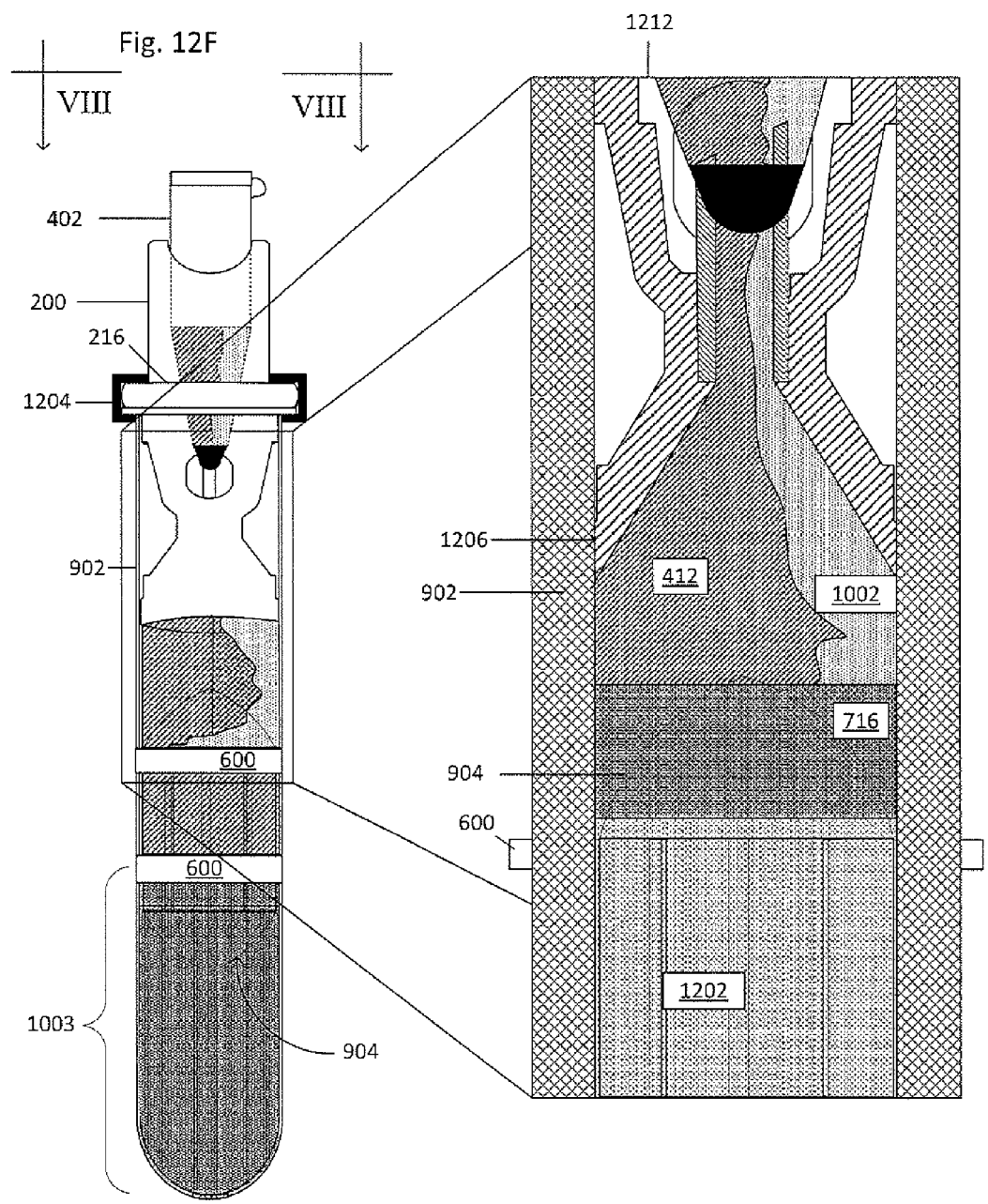
Figure 12G:
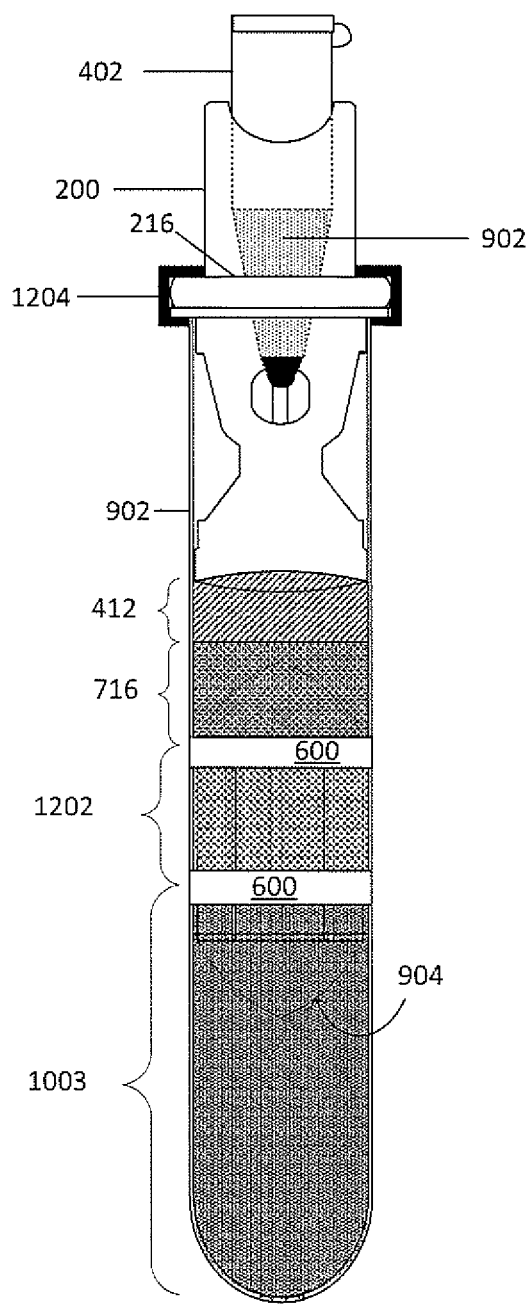

Returning to FIG. 8, in block 814, the fluid layering device 700 is removed from the collector 200 and a processing vessel 402 including the collection fluid 412 is inserted into the collector 200, as also shown in FIG. 12E. The layering fluid 716 added by the fluid layering device 700 fills any air gap that exists extending from the cannula 216 of the collector to the uppermost layer of fluid or sample material within the primary vessel 902. It should be noted that the collection fluid 412 and the layering fluid 716 may be the same type of fluid or may be a different type of fluid. The collection fluid 412 and the layering fluid 716 are referenced differently herein, even when the collection fluid 412 and the layering fluid 716 are the same, to depict that the collection fluid 412 and the layering fluid 716 are introduced to the system and method by different mechanisms, vessels, or devices.

Returning to FIG. 8, in block 816, the vessel, the collector, and the processing receptacle are centrifuged. During centrifugation, the additional collection fluid 412 moves from the processing vessel 402 into the primary vessel 902 via the cannula 216 of the collector 200 and displaces the buffy coat 1002 from the primary vessel 902 into the processing vessel 402 via cannula 216 the collector 200. The processing vessel 402, now including the buffy coat 1002, may be removed from the collector 200.

The collection fluid may be miscible or immiscible with the suspension fluid and inert with respect to the suspension materials. The collection fluid 412 has a greater density than the density of the target material of the suspension (the density may be less than the density of at least one other suspension fraction or the density may be greater than all of the suspension fractions) and is inert with respect to the suspension materials. Examples of suitable collection fluids include, but are not limited to, solution of colloidal silica particles coated with polyvinylpyrrolidone (e.g. Percoll), polysaccharide solution (e.g. Ficoll), iodixanol (e.g. OptiPrep), a complex, branch glucan (e.g. Dextran), cesium chloride, sucrose, sugar-based solutions, polymer-based solutions, surfactants, an organic solvent, a liquid wax, an oil, olive oil, mineral oil, silicone oil, and ionic liquids; perfluoroketones, such as perfluorocyclopentanone and perfluorocyclohexanone, fluorinated ketones, hydrofluoroethers, hydrofluorocarbons, perfluorocarbons, perfluoropolyethers, silicon and silicon-based liquids, such as phenylmethyl siloxane.

The processing receptacle 302 may also include a processing solution to effect a transformation on the target material when the target material enters the processing receptacle 302. The processing solution may be a preservative, a fixative, a cell adhesion solution, a dye, a freezing stabilization media, or the like. Unlike the collection fluid, most, if not all, of the processing solution remains within the processing receptacle 302 upon centrifugation, thereby effecting the transformation on the target material in one manner or another (i.e. preserving, fixing, increasing adhesion properties, or the like) in the processing receptacle 302. The processing solution may be introduced as a liquid or as a liquid container in a casing. The casing may be dissolvable in an aqueous solution but not in the collection fluid (such as a gel cap); or, the casing may be breakable, such that the casing breaks when the processing receptacle 302 is shaken in a vortex mixer. Additionally, more than one processing solution may be used.

Furthermore, when the vessel includes a septum in the closed end, the plasma, for example, may be removed through the septum with a needle, syringe, by draining, or the like. The plasma may then be further processed and analyzed.

Sequential density fractionation is the division of a sample into fractions or of a fraction of a sample into sub-fractions by a step-wise or sequential process, such that each step or sequence results in the collection or separation of a different fraction or sub-fraction from the preceding and successive steps or sequences. In other words, sequential density fractionation provides individual sub-populations of a population or individual sub-sub-populations of a sub-population of a population through a series of steps. For example, buffy coat is a fraction of a whole blood sample. The buffy coat fraction may be further broken down into sub-fractions including, but not limited to, reticulocytes, granulocytes, lymphocytes/monocytes, and platelets. These sub-fractions may be obtained individually by performing sequential density fractionation.

FIG. 13 shows an example method 1300 for retrieving a target material using sequential density fractionation. The example method 1300 is similar to the example method 800, except the example method 1300 collects the target material by sequential density fractionation. After the steps of block A have been performed, as shown in FIG. 8, sequential density fractionation is performed, as seen in block 1302. Block 1302 is also a snapshot of the sequential density fractionation steps. In block 1304, an $n^{th}$ processing receptacle including an $n^{th}$ collection fluid is inserted into the collector, such that $n^{th}$ is greater than or equal to first (i.e. second, third, fourth, and so on). In block 1306, the system is centrifuged to collect a fraction or sub-fraction and the nth processing receptacle is removed. In block 1308, the operator determines whether or not the desired fraction or sub-fraction is obtained. When the desired fraction or sub-fraction is obtained, the process may stop as shown in block 1310, though the process may continue until all fractions or sub-fractions are obtained. When the desired fraction or sub-fractions is not yet obtained, the process restarts at block 1304. The processing receptacles may also include a processing solution to effect a change on the respective sub-fractions. Two or more processing receptacles and respective collection fluids may be used depending on the number of fractions or sub-fractions desired for separation and collection. Each successive collection fluid is denser than the preceding collection fluid. Similarly, each successive fraction or sub-fraction is denser than the preceding fraction or sub-fraction. Once collected, the consecutive sub-fractions may be analyzed, such as for diagnostic, prognostic, research purposes, to determine components characteristics (i.e. a complete blood count), how those characteristics change over time, or the like.

The target material may be analyzed using any appropriate analysis method or technique, though more specifically extracellular and intracellular analysis including intracellular protein labeling; chromogenic staining; molecular analysis; genomic analysis or nucleic acid analysis, including, but not limited to, genomic sequencing, DNA arrays, expression arrays, protein arrays, and DNA hybridization arrays; in situ hybridization ("ISH"—a tool for analyzing DNA and/or RNA, such as gene copy number changes); polymerase chain reaction ("PCR"); reverse transcription PCR; or branched DNA ("bDNA"—a tool for analyzing DNA and/or RNA, such as mRNA expression levels) analysis. These techniques may require fixation, permeabilization, and isolation of the target material prior to analysis. Some of the intracellular proteins which may be labeled include, but are not limited to, cytokeratin ("CK"), actin, Arp2/3, coronin, dystrophin, FtsZ, myosin, spectrin, tubulin, collagen, cathepsin D, ALDH, PBGD, Akt1, Akt2, c-myc, caspases, survivin, $p27^{kip}$, FOXC2, BRAF, Phospho-Akt1 and 2, Phospho-Erk1/2, Erk1/2, P38 MAPK, Vimentin, ER, PgR, PI3K, pFAK, KRAS, ALKH1, Twist1, Snail1, ZEB1, Fibronectin, Slug, Ki-67, M30, MAGEA3, phosphorylated receptor kinases, modified histones, chromatin-associated proteins, and MAGE. To fix, permeabilize, or label, fixing agents (such as formaldehyde, formalin, methanol, acetone, paraformaldehyde, or glutaraldehyde), detergents (such as saponin, polyoxyethylene, digitonin, octyl β-glucoside, octyl β-thioglucoside, 1-S-octyl-β-D-thioglucopyranoside, polysorbate-20, CHAPS, CHAPSO, (1,1,3,3-Tetramethylbutyl)phenyl-polyethylene glycol or octylphenol ethylene oxide), or labeling agents (such as fluorescently-labeled antibodies, enzyme-conjugated antibodies, Pap stain, Giemsa stain, or hematoxylin and eosin stain) may be used.

After collection, the target material may also be imaged or may undergo flow cytometry.

The following is an example method for retrieving a target material when the density of the plasma is changed to be greater than the density of the buffy coat but less than the density of the red blood cells:
  1. Add sample to a tube with a float.
  2. (Optional) Add depletion reagent to the sample.
  3. Centrifuge to effect a density-based separation of the sample and to align the float with a target material.
  4. Apply a first sealing ring to the tube at a location near the lower end of a main body of the float to form a first seal between the tube and the float.
  5. Remove at least a first fraction of the sample from the tube
  6. Add clearing fluid to the tube.

7. Centrifuge to push target material at least above the main body of the float.
8. (Optional) Apply a second sealing ring to the tube at a location near the upper end of the main body of the float to form a second seal between the tube and the float.
9. (Optional) Add fixative and/or permeabilizing agent to the tube to fix and/or permeabilize the target material. Incubation may be performed, if it is desirous to do so.
10. Add at least one stain to the target material (alternatively, the at least one stain may be added with the sample in Step 1).
11. Add density-altering agent to the tube.
12. Insert collector into tube.
13. Insert fluid layering device into collector.
14. Fill any air gap from cannula to uppermost layer of fluid or sample material within the tube with layering fluid via the fluid layering device.
15. Remove fluid layering device and insert processing receptacle including collection fluid into collector.
16. Centrifuge to collect target material.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

We claim:
1. A method comprising the steps of:
providing a primary vessel comprising
an open end, and
a sample comprising a target material and at least one other sample fraction;
adding at least one fluorescent probe to the primary vessel;
adding a density-altering agent to the vessel to change the density of the at least one other sample fraction such that the density of the target material is less than a changed density of the at least one other sample fraction;
inserting a collector into the open end of the primary vessel;
adding a layering fluid to the primary vessel, the layering fluid having a density greater than the target material;
inserting a first processing vessel into the collector, wherein the first processing vessel includes a first collection fluid having a density greater than at least a first sub-fraction of the target material; and
centrifuging the primary vessel, the collector, and the first processing vessel, such that during centrifugation the first collection fluid flows into the primary vessel via a cannula of the collector and at least the first sub-fraction of the target material flows into the first processing vessel via the cannula of the collector,
wherein centrifuging the primary vessel, the collector, and the first processing vessel is performed after inserting the collector into the primary vessel and after inserting the first processing vessel into the collector.

2. The method of claim 1, wherein the density-altering agent is selected from the group consisting of a solution of colloidal silica particles coated with polyvinylpyrrolidone, a polysaccharide solution, iodixanol, a complex branched glucan, cesium chloride, sucrose, a sugar-based solution, a polymer solution, and a multi-phase polymer solution.

3. The method of claim 1, further comprising the steps of:
removing the first processing vessel comprising at least the first sub-fraction from the collector;
inserting a second processing vessel comprising a second collection fluid into the collector; and
re-centrifuging the primary vessel with the collector and the second processing vessel,
wherein the second collection fluid flows into the primary vessel via the cannula of the collector and a second sub-fraction of the target material flows into the second processing receptacle via the cannula of the collector,
wherein the second collection fluid has a density greater than the second sub-fraction and the first collection fluid, and wherein the second sub-fraction has a density greater than the density of the first sub-fraction.

4. The method of claim 3, wherein the removing, inserting, and re-centrifuging steps are repeated with an $n^{th}$ processing vessel including an $n^{th}$ collection fluid, wherein $n^{th}$ is equal to or greater than $3^{rd}$, and wherein the removing, inserting, and re-centrifuging steps are repeated until all desired sub-fractions of the target material are obtained from the sample, wherein each successive collection fluid has a density greater than each preceding collection fluid.

5. The method of claim 1, wherein the first processing vessel includes a plug in a closed end.

6. The method of claim 5, wherein the first processing vessel includes cap to seal an open end.

7. The method of claim 5, wherein the cannula of the collector extends at least partially through the plug.

8. The method of claim 1, wherein adding the layering fluid is performed before inserting the collector into the primary vessel.

9. The method of claim 1, wherein adding the layering fluid is performed after inserting the collector into the primary vessel by inserting a fluid laying device into the collector and forcing the layering fluid through the cannula of the collector and into the primary vessel.

10. The method of claim 1, further comprising the step of adding a depletion reagent to the primary vessel.

11. The method of claim 10, wherein the depletion reagent lyses at least one non-target material.

12. The method of claim 10, wherein the depletion reagent changes the density of at least one non-target material.

13. The method of claim 1, wherein the first collection fluid and the layering fluid are selected from the group consisting of: a solution of colloidal silica particles coated with polyvinylpyrrolidone, a polysaccharide solution, iodixanol, an organic solvent, a liquid wax, an oil, a gas, olive oil, silicone oil, immersion oil, mineral oil, paraffin oil, silicon oil, fluorosilicone, perfluorodecalin, perfluoroperhydrophenanthrene, perfluorooctylbromide, 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, ionic liquids, a polymer-based solution, a surfactant, a perfluoroketone, perfluorocyclopentanone, perfluorocyclohexanone, a fluorinated ketone, a hydrofluoroether, a hydrofluorocarbon, a perfluorocarbon, a perfluoropolyether, silicon, a silicon-based liquid, phenylmethyl siloxane, and combinations thereof.

14. The method of claim 1, the primary vessel further comprising a float comprising a main body.

15. The method of claim 14, further comprising the step of centrifuging the primary vessel comprising the sample and the float thereby effecting a density-based separation of the sample into the target material and the at least one other sample fraction and trapping the target material between the main body of the float and an inner wall of the primary vessel,
  wherein the centrifuging to effect the density-based separation is performed after providing the primary vessel comprising the sample and the float, and before adding the at least one fluorescent probe.

16. The method of claim 15, further comprising the step of adding a clearing fluid having a density greater than the target material to the primary vessel, wherein the clearing fluid is added to the primary vessel after centrifuging to effect the density-based separation.

17. The method of claim 16, further comprising the step of forming a first seal between a lower end of the main body of the float and the inner wall of the primary vessel, wherein forming the first seal is performed after centrifuging to effect the density-based separation and before adding clearing fluid.

18. The method of claim 17, further comprising the step of moving the target material at least above the main body of the float by re-centrifuging the primary vessel, wherein the moving step is performed after the adding the clearing fluid, after centrifuging to effect the density-based separation, and before adding the at least one fluorescent probe.

19. The method of claim 18, further comprising the step of forming a second seal between an upper end of the main body of the float and the inner wall of the primary vessel, wherein forming the second seal is performed after the moving step and before adding the at least one fluorescent probe to the primary vessel.

* * * * *